United States Patent
Paraluppi et al.

(10) Patent No.: US 10,441,701 B2
(45) Date of Patent: Oct. 15, 2019

(54) MEDICAL APPARATUS FOR THE PREPARATION OF MEDICAL FLUID

(71) Applicant: GAMBRO LUNDIA AB, Lund (SE)

(72) Inventors: Marco Paraluppi, Medolla (IT); Stefano Micco, Casalecchio di Reno (IT)

(73) Assignee: Gambro Lundia AB, Lund (SE)

( * ) Notice: Subject to any disclaimer, the term of this patent is extended or adjusted under 35 U.S.C. 154(b) by 283 days.

(21) Appl. No.: 15/500,338

(22) PCT Filed: Jul. 31, 2015

(86) PCT No.: PCT/EP2015/067667
§ 371 (c)(1),
(2) Date: Jan. 30, 2017

(87) PCT Pub. No.: WO2016/016429
PCT Pub. Date: Feb. 4, 2016

(65) Prior Publication Data
US 2017/0209635 A1    Jul. 27, 2017

(30) Foreign Application Priority Data
Jul. 31, 2014   (EP) .................................... 14179361

(51) Int. Cl.
*A61M 1/16*    (2006.01)
*A61M 1/34*    (2006.01)
*A61M 1/36*    (2006.01)

(52) U.S. Cl.
CPC .......... *A61M 1/1668* (2014.02); *A61M 1/168* (2013.01); *A61M 1/169* (2013.01);
(Continued)

(58) Field of Classification Search
CPC .. A61M 1/1656; A61M 1/1668; A61M 1/169; A61M 1/3643; A61M 2209/082
See application file for complete search history.

(56) References Cited

U.S. PATENT DOCUMENTS

| | | | |
|---|---|---|---|
| 6,428,706 B1 * | 8/2002 | Rosenqvist | A61M 1/1656 210/232 |
| 2009/0215283 A1 | 8/2009 | Du | |

(Continued)

FOREIGN PATENT DOCUMENTS

| | | |
|---|---|---|
| EP | 0458041 | 11/1995 |
| EP | 1049497 | 1/2008 |

(Continued)

OTHER PUBLICATIONS

PCT International Search Report and Written Opinion for PCT/EP2015/067667 dated Sep. 24, 2015 (11 pages).

*Primary Examiner* — Leslie R Deak
(74) *Attorney, Agent, or Firm* — Mueting, Raasch & Gebhardt, P.A.

(57) ABSTRACT

A medical apparatus for the preparation of medical fluid is disclosed, comprising a support structure, a movable member, biasing means, and locking means. The movable member is mounted to the support structure and the biasing means are configured to operate in at least one of a repulsion mode and an attraction mode In the repulsion mode, the biasing means exert on the movable member a biasing force directing the movable member away from its retracted configuration, and in the attraction mode, the biasing means exert on the movable member a biasing force directing the movable member towards its retracted configuration. A blood treatment apparatus comprising the medical apparatus for the preparation of fluid, a method of setting up the medical apparatus, and a method for use of the apparatus are also disclosed.

30 Claims, 9 Drawing Sheets

(52) U.S. Cl.
CPC ........ *A61M 1/1656* (2013.01); *A61M 1/1682* (2014.02); *A61M 1/342* (2013.01); *A61M 1/3626* (2013.01); *A61M 1/3643* (2013.01); *A61M 2205/502* (2013.01); *A61M 2209/082* (2013.01)

(56) References Cited

U.S. PATENT DOCUMENTS

| | | |
|---|---|---|
| 2010/0162523 A1 | 7/2010 | Ferguson |
| 2012/0007705 A1 | 1/2012 | Fullerton |
| 2013/0175905 A1 | 7/2013 | Sanlaville |

FOREIGN PATENT DOCUMENTS

| | | |
|---|---|---|
| EP | 2735321 | 5/2014 |
| WO | WO 97/02056 | 1/1997 |
| WO | WO 99/37342 | 7/1999 |
| WO | WO 2011/037845 | 3/2011 |
| WO | WO 2012/162515 | 11/2012 |

\* cited by examiner

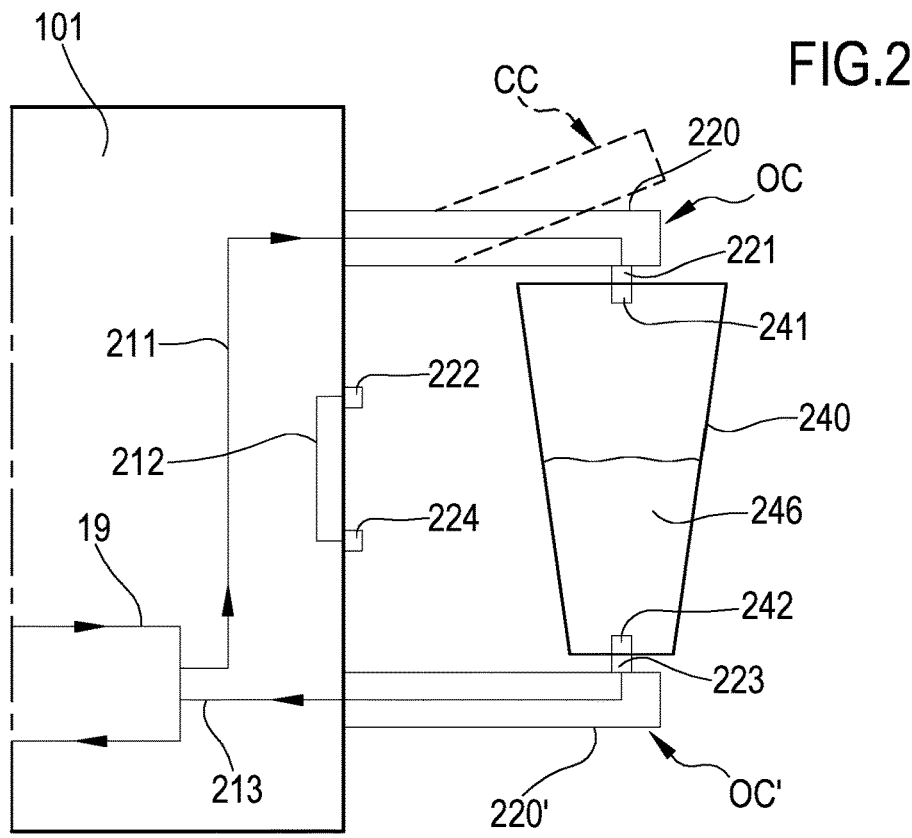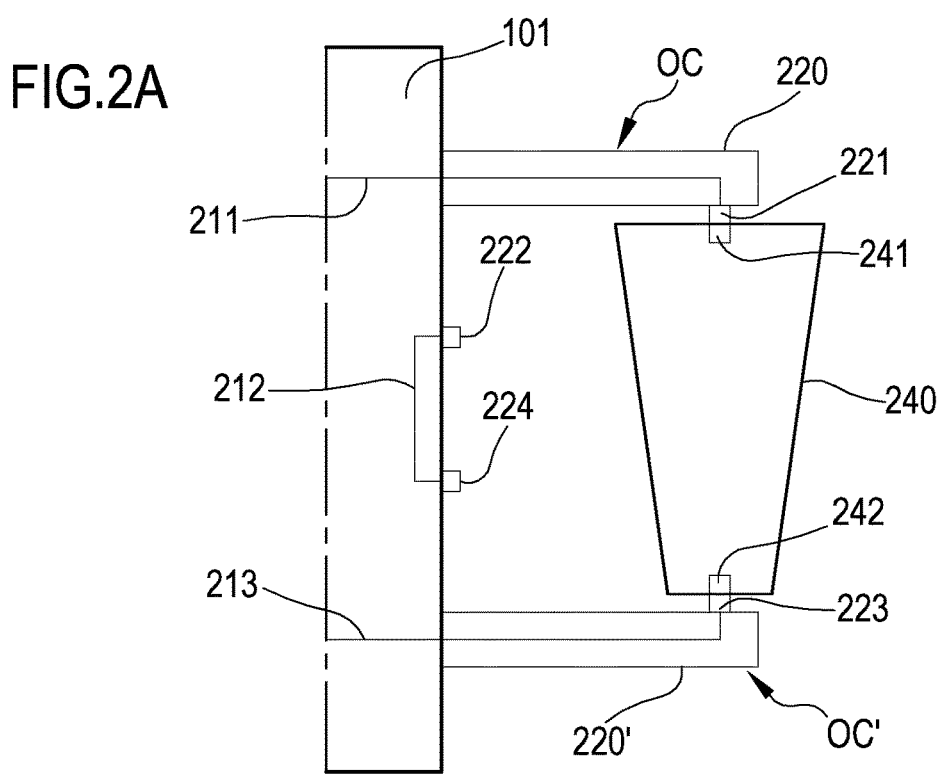

MEDICAL APPARATUS FOR THE PREPARATION OF MEDICAL FLUID

This application is a U.S. National Stage Application of International Application No. PCT/EP2015/067667, filed Jul. 31, 2015, which was published in English on Feb. 4, 2016 as International Publication No. WO 2016/016429 A1. International Application No. PCT/EP2015/067667 claims priority to European Application No. 14179361.2 filed Jul. 31, 2014.

FIELD OF THE INVENTION

The present invention relates to a medical apparatus for the preparation of medical fluid, in particular replacement fluid and/or dialysis fluid. In accordance with certain aspects, the medical apparatus according to the invention comprises a system for coupling a substitutable container to the medical apparatus. The invention also pertains to a method of coupling a substitutable container to the medical apparatus.

In the present document, the concept of a substitutable container is understood to include disposable or reusable containers designed for single or multiple use, substitutable containers designed for replacement upon depletion and re-use when refilled, and other containers capable of single or multiple use in supplying one or more substances. Substitutable containers may be rigid or deformable (such as bags). The terms "container" and "cartridge" as used in this document are understood to include the concept of substitutable containers without necessitating an explicit reference thereto.

BACKGROUND ART

Preparation of medical fluid for extracorporeal blood treatment typically involves adding one or more substances (e.g. NaCl or CaCl) to a base fluid (e.g. water). The base fluid is typically drawn from a fluid source, for example a fluid line or a tank. One or more substances are then added to the fluid, typically by conveying at least a portion of the fluid through one or more substitutable containers holding the one or more substances.

The adding of substances may be achieved in several separate stages, where one or more substances are added to the fluid at each stage. The stages are typically arranged in series such that fluid prepared at one stage is subsequently conveyed through another stage. However, other layouts or setups are possible (e.g. stages being arranged in parallel).

At each stage, typically, a flow controller (e.g. a valve or a pump) conveys a predetermined amount of fluid into and/or through the container, thereby dissolving or otherwise carrying a desired amount of the substance or substances present in the container with the fluid and out of the container. The containers typically contain the one or more substances as salts or liquids. After at least a portion of the fluid has been directed through the container and has dissolved an amount of the one or more substances and has exited the container, the fluid is mixed with the remainder of the fluid in a common or main fluid line. In cases where separate sources of fluids are used (e.g. a main fluid source providing the main fluid flow, and a separate fluid source supplying fluid to one or more stages) the fluid exiting a stage is then mixed with the base fluid coming from a (separate) main fluid source.

Downstream from the stage or stage(s), typically, one or more sensors (e.g. conductivity sensors, optical sensors, or other) are arranged so as to measure the concentration of the one or more substances in the fluid. Based on the concentration(s) measured, the respective flow controller(s) may be controlled to increase or decrease the respective flow of fluid through the respective container in order to achieve and/or maintain a desired concentration of each of the one or more substances.

Downstream from the last stage, typically, one or more filters (e.g. ultrafilters) are employed in order to remove any unwanted particles and/or substances in the fluid. Typically, at least two filters are employed in order to provide two-stage safety and avoid a single point of failure. In particular, when infusion fluid is prepared and provided for pre- and/or post-dilution, at least two ultrafilters are employed to provide infusion fluid having the required composition and purity for being infused into the vascular system of a patient.

The one or more substances are typically provided (e.g. in the form of salt or dry or wet concentrate) in a cartridge or container that is designed to operably couple to the preparation apparatus. The containers are provided with an inlet port and an outlet port, thereby allowing a fluid to enter the container, to dissolve or otherwise take up some of its contents, and to exit the container.

The container or containers are installed before fluid preparation commences and/or replaced during fluid preparation, for example when their contents are depleted. The installation or coupling requires the apparatus to have a corresponding coupling system.

Before installation of the containers and/or after preparation of fluid (e.g. before storage or when a unit is scheduled for downtime), the fluid lines of the apparatus require priming and/or cleaning, disinfection, etc. During the respective process (e.g. priming), typically no containers are installed at the different stages. In order to facilitate the process, the respective coupling ports (which would be connected to respective inlet and outlet ports of a container during operation) need to be connected to a bypass line of some kind, so that fluid (e.g. priming fluid) can pass through the respective main lines, branch lines, and connectors.

In some examples, the coupling system includes two arms pivotably connected to the apparatus and each carrying a coupling port configured for coupling with a corresponding inlet or outlet port of the cartridge or container. The two arms are further capable of assuming at least a retracted position, in which the coupling port is connected to a corresponding bypass port and a bypass line of the apparatus. This position allows for priming, disinfection, cleaning, or other procedures when no container is installed and/or when the apparatus is not in operation (e.g. preparing a fluid). Also, if the apparatus comprises several stages for the optional installation of several containers, not all stages need to be in use, depending upon the type of fluid to be prepared.

A single two-arm stage typically has a single bypass line comprising two bypass ports, wherein the two arms may be positioned or configured so that the coupling ports are secured and connected to the bypass ports, thereby defining a closed loop from a bifurcation on the main fluid line where fluid is drawn, through an intake line and a pump, as well as through the coupling port, bypass port, bypass line, another bypass port, another coupling port, and through an outlet line back to another bifurcation, feeding the fluid back into the main fluid line.

In the retracted position, a proper connection between the coupling ports and the bypass ports needs to be ensured, so that no fluid can leak from the circuit and no foreign substances can contaminate fluid flowing through the circuit.

In order to ensure a proper connection the coupling ports and the bypass ports, different systems have been devised. In one example, a proximity sensor (e.g. a reed switch) is configured to sense the proximity of the arm carrying the coupling port, generating a corresponding signal for a control unit to process. In another example, a mechanical switch (e.g. a micro switch) is actuated upon the arm carrying the coupling port being locked into proper position.

A key issue of known systems includes a proper adjustment or calibration of the sensors. On one hand, the system should ensure that an improperly configured arm is accurately detected, so that operating personnel may be made aware of an inadequate connection between any of the coupling ports and bypass ports. On the other hand, false alarms should be avoided as much as possible, such that the apparatus can be operated with a high efficiency.

Proximity switches need to be properly positioned and configured in order to detect the position of an arm with the required accuracy and reliability. Mechanical switches also require proper placing and adjustment and are prone to contamination by foreign substances (e.g. dust, dirt, particles). Mechanical switches may also be difficult to clean.

EP 0458041 discloses an apparatus for preparation of dialysis fluid in connection with haemodialysis and for preparation of replacement fluid in connection with haemofiltration or haemodiafiltration, which has lever arms and a by-pass line.

EP 1049497 discloses a holder for a powder cartridge in a dialysis machine and describes safety considerations in connection with the holder and the use of powder cartridges. Separate holders for the cartridges are also described. Sensors can detect whether the holders are folded out and contain a cartridge.

It is an object of the present invention to render available an apparatus for the preparation of fluids designed to limit improper positioning of the one or more movable members configured to hold the container of one or more substances.

Additionally, it is an auxiliary object of the invention an apparatus configured to allow reliably detecting an incorrect configuration (e.g. if one or more movable members are not properly locked in their retracted position), thereby ensuring proper connection of the corresponding ports and preventing contamination of the circuit and leakage of fluids.

It is a further object of the invention to render available an apparatus, which reduces the number of false alarms and improves the rate of detection (e.g. minimizing failed detections).

It is a further object of the invention to provide a method of setting up a medical apparatus for the preparation of fluids, which improves the reliability of the process of connecting and disconnecting containers.

It is a further object of the invention to provide a method of using a medical apparatus for the preparation of fluids.

It is a further object of the invention to render available an extracorporeal blood treatment apparatus comprising a medical apparatus for the preparation of fluids.

SUMMARY

At least one of the above objects is substantially reached by an apparatus or by an assembly according to one or more of the appended claims.

At least one of the above objects is substantially reached by a method according to one or more of below described aspects.

An apparatus and assemblies for the extracorporeal treatment of blood according to aspects of the invention are here below described.

In a $1^{st}$ aspect there is provided a medical apparatus for the preparation of medical fluid, comprising a support structure, a movable member, movably mounted to the support structure and carrying a first port, a first fluid line carried by the support structure and configured to be put into fluid communication with a source of fluid, the first fluid line being in fluid communication with the first port, a second fluid line carried by the support structure and being in fluid communication with a second port, biasing means, and locking means. The first port is configured to receive a first connection port of a container of at least one substance to be added to a fluid coming from the source of fluid. The movable member is mounted to the support structure for movement between at least a retracted configuration, in which the first port and the second port are coupled to each other, and an unretracted configuration, in which the first port and the second port are spaced apart from each other. The locking means are configured to releasably hold the movable member in its retracted configuration. The biasing means are configured to operate in at least one of a repulsion mode and an attraction mode. In their repulsion mode, the biasing means are configured to exert on the movable member, at least when the locking means release the movable member from its retracted configuration, a biasing force directing the movable member away from its retracted configuration. In their attraction mode, the biasing means are configured to exert on the movable member, at least when the movable member is in its unretracted configuration, a biasing force directing the movable member towards its retracted configuration.

In a $2^{nd}$ aspect according to the $1^{st}$ aspect, the biasing means are configured to operate only in their repulsion mode and to exert on the movable member a biasing force directing the movable member away from its retracted configuration and towards its unretracted configuration.

In a $3^{rd}$ aspect according to the $1^{st}$ or $2^{nd}$ aspect, the biasing means are configured to operate only in their repulsion mode and to exert on the movable member a biasing force causing the movable member to move to its unretracted configuration when the locking means release the movable member.

In a $4^{th}$ aspect according to any one of aspects 1 to 3, when the movable member is in its retracted configuration, the first and second ports are configured to put the first and second fluid lines in fluid communication with each other.

In a $5^{th}$ aspect according to any one of aspects 1 to 4, the support structure carries the second port.

In a $6^{th}$ aspect according to the $1^{st}$, $4^{th}$, or $5^{th}$ aspect, the biasing means are configured to operate only in their attraction mode and comprise a first magnetic element and a ferromagnetic element, the first magnetic element being configured to exert the biasing force based on the ferromagnetic element being subjected to a magnetic attraction exerted by the first magnetic element.

In a $7^{th}$ aspect according to any one of aspects 1 to 5, the biasing means comprise a first magnetic element and a second magnetic element, the first and second magnetic elements being configured to exert the biasing force.

In an $8^{th}$ aspect according to the $7^{th}$ aspect, the first magnetic element is carried by the movable member and/or the second magnetic element is carried by the support structure, optionally the first magnetic element and/or the second magnetic element comprising one of: a solenoid and a bar magnet.

In a 9th aspect according to any one of aspects 1 to 5, the biasing means are configured to operate only in the repulsion mode and comprise a mechanical element configured to exert the biasing force.

In a 10th aspect according to the 9th aspect, the mechanical element is operably interposed between the support structure and the movable member. Optionally, the mechanical element comprises one of a spring, a torsion spring, and an elastically deformable plastic element.

In an 11th aspect according to any one of aspects 1 to 10, the locking means comprise a first locking element configured to selectively engage with a second locking element. The first locking element is carried by the movable member and the second locking element is carried by the support structure. At least one of the first and second locking elements is elastically biased.

In a 12th aspect according to the 11th aspect, at least one of the first and second locking elements is configured to be movable with respect to the other of the first and second locking elements in order to achieve selective engagement.

In a 13th aspect according to any one of aspects 1 to 12, the medical apparatus further comprises a sensor configured to generate a signal indicative of a configuration of the movable member.

In a 14th aspect according to any one of aspects 1 to 12, the medical apparatus further comprises a sensor configured to generate at least a first signal when the movable member is in its retracted configuration and a second signal, different from the first signal, when the movable member is in its unretracted configuration.

In a 15th aspect according to the 14th aspect, the medical apparatus further comprises a control unit configured to receive the first and second signals from the sensor to discriminate between the first and second signals and to generate an output signal based on the outcome of the discrimination. The apparatus optionally includes a user interface connected to the control unit. The output signal is configured to cause display on the user interface of an indicium indicative of a current configuration of the movable member.

In a 16th aspect according to any one of aspects 1 to 15, the movable member is mounted to the support structure in a manner that allows for a pivoting movement of the movable member with respect to the support structure. Optionally, at least a retracted angular position relative to the support structure of the movable member in its retracted configuration is different from an unretracted angular position relative to the support structure of the movable member in its unretracted configuration.

In a 17th aspect according to any one of aspects 1 to 16, the medical apparatus further comprises a third port, a third fluid line carried by the support structure, the third fluid line being in fluid communication with the third port, and a fourth port in fluid communication with the second fluid line and connected to an end of the second fluid line opposite to the second port.

In an 18th aspect according to the 17th aspect, the third port is carried by the movable member. When the movable member is in its retracted configuration, the third port and the fourth port are connected to each other. When the movable member is in its unretracted configuration, the third port and the fourth port are spaced apart from each other.

In a 19th aspect according to the 18th aspect, when the movable member is in its retracted configuration, the third and fourth ports put the second and third fluid lines in fluid communication with each other.

In a 20th aspect according to the 16th aspect, the medical apparatus further comprises a second movable member, movably mounted to the support structure and carrying the third port, second biasing means, and second locking means. The second movable member is mounted to the support structure for movement between at least a retracted configuration of the second movable member, in which the third port and the fourth port are connected to each other, and an unretracted configuration of the second movable member, in which the third port and the fourth port are spaced apart from each other. The second locking means are configured to releasably hold the second movable member in its retracted configuration. The second biasing means are configured to operate in at least one of a repulsion mode and an attraction mode. In their repulsion mode, the second biasing means exert on the second movable member, at least when the second locking means release the second movable member from its retracted configuration, a second biasing force directing the second movable member away from its retracted configuration. In their attraction mode, the second biasing means are configured to exert on the second movable member, at least when the second movable member is in its unretracted configuration, a second biasing force directing the second movable member towards its retracted configuration.

In a 21st aspect according to the 20th aspect, the second biasing means are configured to operate only in their repulsion mode to exert a biasing force causing the second movable member to move away from its retracted configuration to its unretracted configuration when the second locking means release the second movable member.

In a 22nd aspect according to any one of aspects 19 or 20, when the second movable member is in its retracted configuration, the third and fourth ports are configured to put the second and third fluid lines in fluid communication with each other.

In a 23rd aspect according to any one of aspects 19 to 22, the support structure carries the fourth port.

In a 24th aspect according to any one of aspects 19 to 23, the fourth port is configured to receive a second connection port of the container.

In a 25th aspect according to the 24th aspect, the medical apparatus further comprises a main fluid line having a first end defining a main inlet port configured to be put into fluid communication with the source of fluid and a second end defining a main outlet port. The main fluid line further comprises a first bifurcation, the first bifurcation putting the first fluid line into fluid communication with the main fluid line.

In a 26th aspect according to any one of aspects 1 to 25, the first fluid line comprises a first flow controller configured to control flow of fluid between the main fluid line and the first port.

In a 27th aspect according to the 26th aspect, the first flow controller comprises one of a pump, a peristaltic pump, and a valve.

In a 28th aspect according to any one of aspects 24 to 26 and according to any one of aspects 16 to 23, the medical apparatus further comprises a second bifurcation putting the third fluid line into fluid communication with the main fluid line, and optionally a second flow controller configured to control flow of fluid between the third port and the main fluid line.

In a 29th aspect according to any one of aspects 24 to 26, the medical apparatus further comprises an output tank connected to the main outlet port and configured for collecting a pre-fixed amount of fluid from the main fluid line, optionally the tank having an internal volume of equal to or greater than 5 liters.

In a 30th aspect according to any one of aspects 1 to 29, the medical apparatus further comprises one or more containers.

In a 31st aspect, there is provided a method of setting up an apparatus for the preparation of medical fluid according to any one of the aspects 1 to 30, comprising the steps of releasing the movable member from its retracted configuration, moving the movable member into its coupling configuration, placing a first container in a coupling position with respect to the movable member, and moving the movable member from its coupling configuration into its operating configuration.

In a 32nd aspect according to the 31st aspect, the method comprises the steps of moving the movable member from its operating configuration into its coupling configuration, removing the first container from the apparatus, placing a second container in a coupling position with respect to the movable member, and moving the movable member from its coupling configuration into its operating configuration.

In a 33rd aspect according to the 30th aspect, the method further comprises the steps of moving the movable member from its operating configuration into its coupling configuration, removing the first container from the apparatus, and moving the movable member from its coupling configuration into its retracted configuration.

In a 34th aspect according to the 33rd aspect, the method further comprises, after moving the movable member from its coupling configuration into its retracted configuration, initiating one of a priming process, a disinfection process, and a cleaning process.

In a 35th aspect according to any one of aspects 30 to 33, the method further comprises the steps of detecting a current configuration of the movable member, and providing a status signal indicative of the current configuration of the movable member and based on the detected current configuration of the movable member.

In a 36th aspect, there is provided a use of a medical apparatus for the preparation of medical fluid according to any one of claims 1 to 30 in preparing medical fluid. The medical fluid optionally comprises one of replacement fluid and dialysis fluid.

In a 37th aspect, there is provided an extracorporeal blood treatment apparatus, comprising at least one of a dialysis fluid line configured to be connected to an inlet of a dialysis fluid chamber of a blood treatment unit, a fluid replacement line configured to be connected to an extracorporeal blood circuit or directly to a cardiovascular system of a patient, a waste line connected to an outlet of the dialysis fluid chamber, and a medical apparatus for the preparation of medical fluid according to any one of aspects 1 to 30 connected to supply fluid to at least one of the dialysis fluid line and the replacement fluid line.

In a 38th aspect according to the 37th aspect, the extracorporeal blood treatment apparatus further comprises a replacement fluid line. The replacement fluid line comprises one or more of a pre-dilution line connected to the blood withdrawal line downstream from the blood pump, a post-dilution line connected to the blood return line, and a pre-blood pump infusion line connected to the blood withdrawal line upstream from the blood pump.

DESCRIPTION OF THE DRAWINGS

Aspects of the invention are shown in the attached drawings, which are provided by way of non-limiting example, wherein:

FIG. 2 schematically shows a first embodiment of a coupling system for a container 240 in accordance with the present invention;

FIGS. 2A and 2B schematically show movable members 220 and 220' in an operating configuration (see FIG. 2A) and in a retracted configuration (FIG. 2B);

FIG. 5 shows movable member 220 in the coupling configuration CC and container 240 also in cross section;

FIG. 6 shows the same configuration as the cross section of FIG. 5;

DETAILED DESCRIPTION

Figure 1:
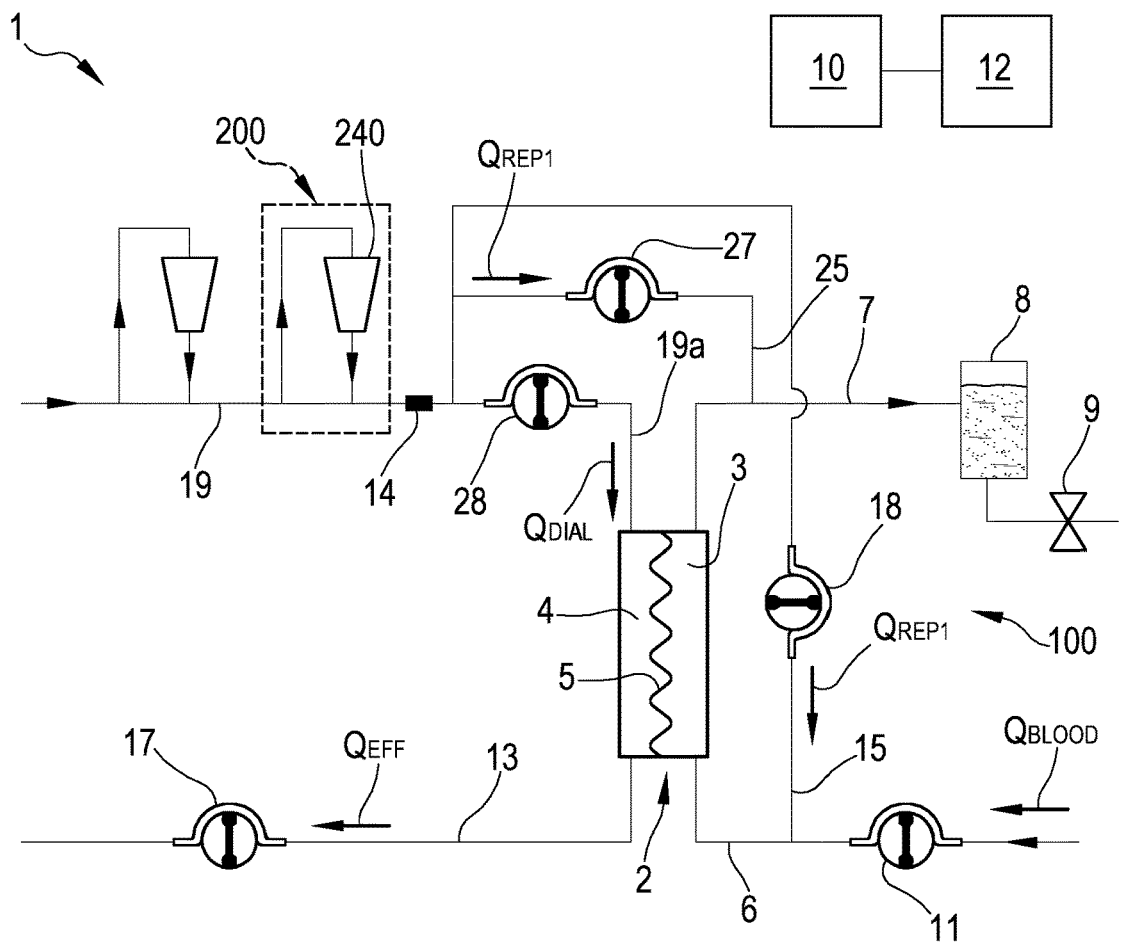
FIG. 1 schematically shows an example of a blood treatment apparatus comprising an apparatus for the preparation of medical fluid.

FIG. 1 shows an exemplary and non-limiting embodiment of an apparatus for extracorporeal treatment of blood comprising an apparatus for the preparation of medical fluid. FIG. 1 schematically shows an example of a blood treatment apparatus 1 designed for delivering any one of the following treatments: hemodialysis, hemofiltration, hemodiafiltration, and ultrafiltration.

The apparatus 1 comprises a treatment unit 2 having a primary chamber 3 and a secondary chamber 4 separated by a semipermeable membrane 5. Depending upon the treatment, the membrane of the treatment unit may be selected to have different properties and performances. A blood withdrawal line 6 is connected to an inlet of the primary chamber 3, and a blood return line 7 is connected to an outlet of the primary chamber 3. The blood withdrawal line, the primary chamber 3, and the blood return line 7 are part of an extracorporeal blood circuit 100. In use, the extracorporeal blood circuit 100 is mounted on a support structure 101 (shown in FIG. 2) of the apparatus 1. The support structure 101 may be a front or a side panel of a main body of the apparatus 1. Support structure 101 may also be a structure fitted to a front or side panel of a main body of apparatus 1.

In use, the blood withdrawal line 6 and the blood return line 7 are connected to a needle or to a catheter or other access device (not shown) which is then placed in fluid communication with the patient vascular system, such that blood can be withdrawn through the blood withdrawal line, passed through the primary chamber and then returned to the patient's vascular system through the blood return line 7.

An air separator, such as bubble trap 8 may be present on the blood return line 7. Moreover, a safety clamp or valve 9 controlled by a control unit 10 may be present on the blood return line 7, for example downstream from the bubble trap. It is noted that for reasons of clarity, control connections from control unit 10 to individual components are not shown in FIG. 1. It is understood that control unit 10 may be connected to practically all components of apparatus 1, for example valves, pumps, sensors, user interfaces, communications devices, or any other components either supplying information to control unit 10 or receiving information therefrom.

A bubble sensor, for example associated with bubble trap 8 or coupled to a portion of line 7 between bubble trap 8 and clamp 9 may be present. If present, the bubble sensor is connected to the control unit 10 and is configured to send to the control unit 10 signals for the control unit to cause closure of clamp 9 in case one or more bubbles above predetermined safety thresholds are detected.

As shown in FIG. 1, the blood flow $Q_{BLOOD}$ through the blood lines is controlled by a blood pump 11, for example a peristaltic blood pump, acting either on the blood withdrawal line (as shown in FIG. 1) or on the blood return line. An operator may enter a set value for the blood flow rate $Q_{BLOOD}$ through a user interface 12, and the control unit 10, during treatment, may be configured to control the blood pump based on the set blood flow rate. The control unit 10 may comprise one or more digital processors (CPU) and respective memory (or memories), an analog circuit, or a combination thereof.

An effluent fluid line 13 is connected, at one end, to an outlet of the secondary chamber 4 and, at another end, to a waste outlet, for example comprising an effluent fluid container collecting the fluid extracted from the secondary chamber or a drainage line. The circuit shown in FIG. 1 may also present a pre-dilution fluid line 15 connected to the blood withdrawal line. Fluid line 15 may supply replacement fluid from an infusion fluid source, for example an apparatus for the preparation of medical fluid in accordance with the present invention, to an extracorporeal blood circuit.

It is noted that alternatively or in addition to pre-dilution fluid line 15, the apparatus of FIG. 1 may include a post-dilution fluid line 25 which may be connected to the blood return line 7 either at or upstream the bubble trap 8 (as shown in FIG. 1), or downstream the bubble trap (e.g. downstream clamp 9). The post-dilution line 25 connects an infusion fluid source to the blood return line. As mentioned, the apparatus of FIG. 1 may include both a pre-dilution fluid line 15 and a post infusion fluid line 25. In this case, the two infusion fluid lines may receive infusion fluid from a same source of infusion fluid. Additionally, the apparatus 1 may present a further infusion line connected, at one end, with a portion of blood withdrawal line 6 positioned upstream the blood pump 11 and, at its other end, with a infusion fluid source, which, for example, may contain a drug, or a regional anticoagulant such as a citrate solution, or a nutrient solution or other. This further infusion line is herein referred to as pre-blood pump infusion line. The apparatus of FIG. 1, further includes a dialysis fluid line 19a connected at one end with a source of medical fluid and at its other end with the inlet of the secondary chamber 4 of the treatment unit.

Although the exemplifying apparatus shown in FIG. 1 illustrates fluid lines 13, 19, 19a, 15, and 25, none of the illustrated elements is understood as limiting. In fact the apparatus 1 may be of the type having any combination of the above-described lines. For example apparatus 1 may include only the effluent line 13 and the dialysis fluid line 19a. Alternatively, apparatus 1 may include the pre-dilution infusion line 15 and/or the post-dilution infusion line 25 in addition to the effluent line 13 and the dialysis fluid line 19a.

Depending upon the type of apparatus 1, and thus depending upon the number and type of lines present, corresponding pumps may be present or not. An effluent fluid pump 17 operates on effluent fluid line 13 under the control of control unit 10 to regulate the flow rate $Q_{EFF}$ across the effluent fluid line 13. If the apparatus has a pre-dilution line 15, then a pre-infusion pump 18 acts on pre-dilution infusion line 15 to regulate the flow rate $Q_{REP1}$ through the same pre-dilution infusion line. If the apparatus has a post-dilution line 25, then a post-infusion pump 27 acts on post-dilution infusion line 25 to regulate the flow rate $Q_{REP2}$ through the same post-dilution infusion line. It is noted that in case of two infusion lines being present (pre-dilution line 15 and post-dilution 25), each infusion line may cooperate with a respective infusion pump 18, 27.

A dialysis fluid pump 28 works on the dialysis fluid line 19a under the control of control unit 10, in order to supply fluid from the medical fluid source to the secondary chamber at a flow rate $Q_{DIAL}$. The dialysis fluid pump 28, the infusion fluid pump or pumps 18, 27 and the effluent fluid pump 17 are operatively connected to control unit 10 which controls the pumps. The pump control may be carried out by the control unit based on set values of desired flow rates through the above lines as entered by the user or as pre-stored in a memory connected to the control unit 10.

It is noted that individual flow rates through the above-described lines or at least an overall weight loss rate may be determined using sensors. For example, Coriolis mass flow sensors, mechanical flow sensors, electromagnetic flow sensors, volumetric flow sensors may be used in order to detect or allow detection by the control unit of the actual flow rate through each of the above lines. The medical fluid is produced online by the apparatus 200 and then supplied to the extracorporeal blood circuit (in case of replacement fluid) and to the second chamber 4 of the treatment unit 2 (in case of dialysis fluid).

The concentration of one or more substances in the medical fluid supplied through medical fluid line 19 may be measured by sensor 14. Sensor 14 may be arranged on fluid line 19 downstream from fluid preparation. Sensor 14 may comprise any sensor or sensors capable of detecting the concentration of one or more substances in the medical fluid supplied. Sensor 14 may include, for example, a conductivity sensor, an optical sensor, or other sensor(s). Sensor 14 is connected to control unit 10 in order to enable control unit 10 to detect and regulate the supply of one or more substances based on the measured concentration(s). For example, control unit 10 may be configured to increase or decrease the flow of fluid through fluid preparation apparatus 200, typically through a pump, in order to increase or decrease the concentration of the substance or substances supplied by the preparation apparatus 200.

One or more ultrafilters may be arranged downstream of fluid preparation apparatus 200 (not shown in FIG. 1). Typically, at least 2 ultrafilters are used, wherein one ultrafilter is arranged on dialysis fluid line 19a, anywhere between fluid preparation apparatus 200 and treatment unit 2. A second ultrafilter is arranged in the replacement fluid line connecting medical fluid line 19 to pre- and post dilution lines 15 and 25.

Control unit 10 is also connected to a user interface 12, for example a graphic user interface, which receives input from an operator and displays output generated by apparatus 1. For example, the graphic user interface 12 may include a touch screen, a display screen and/or a keyboard for entering user input or a combination thereof.

Figure 1A:
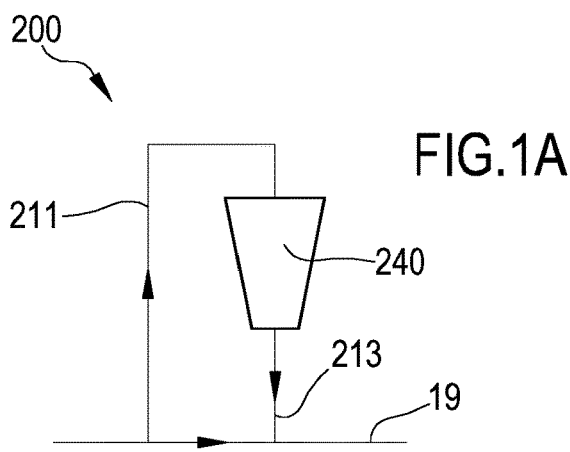
FIG. 1A schematically shows a first example of a fluid preparation apparatus 200 and a corresponding circuit, in which source fluid is drawn directly from medical fluid line 19 of apparatus 1.

FIG. 1A schematically shows a first example of a fluid preparation apparatus 200 and a corresponding fluid preparation circuit, in which source fluid is drawn directly from medical fluid line 19 of apparatus 1. Apparatus 200 comprises an inlet line 211, an outlet line 213, and a coupling system for a container 240 containing one or more substances to be added to fluid drawn through inlet line 211. Medical fluid line 19 is connected at an upstream end thereof to a source of fluid, for example water, and is configured to convey water towards a downstream end thereof. Medical fluid line 19 may have corresponding ports (not shown) at opposite ends thereof, configured to respectively connect medical fluid line 19 to the source of fluid and to a circuit to which the prepared fluid is supplied.

Container 240 may be a substitutable container designed for single (e.g. a disposable container) or multiple (e.g. a reusable container) use, a container designed to be replaced upon depletion and re-used when refilled, or any other container capable of single or multiple use in supplying one or more substances to be added to fluid flowing through apparatus 200. Typically, container 240 is a disposable container exhibiting a first connection port 241 (e.g. an inlet port 241; see FIG. 2) and a second connection port 242 (e.g. an outlet port 242; see FIG. 2) allowing for container 240 to be put in fluid communication with corresponding ports of a coupling system of a fluid circuit, in which fluid may enter an inner volume of container 240 at inlet port 241 and may exit the inner volume of container 240 at outlet port 242. Based on properties (e.g. composition, temperature, flow rate, viscosity) of a fluid supplied through container 240, one or more substances 246 present in container 240 may be introduced into the fluid. It is noted that "inlet" and "outlet" ports (e.g. of containers) may generally be referred to as "connection" ports, not restricting a direction of fluid flow.

During preparation of fluid, means for controlling fluid flow through fluid line 211 (e.g. a pump, typically a peristaltic pump; not shown in FIG. 1A) are configured to control fluid flow through inlet line 211, through container 240, and through outlet line 213 in order to facilitate dissolution or take-up of the substance(s) contained in container 240.

For example, container 240 may contain sodium chloride (NaCl) in crystalline form. Water supplied from the source of fluid and conveyed through inlet line 211 towards container 240 by a pump at a predetermined rate dissolves sodium chloride contained within container 240. The solution is then further conveyed through outlet line 213 and into medical fluid line 19 in order to be supplied to treatment unit 2. A concentration sensor 14 (see, e.g., FIG. 1) typically determines the concentration of sodium chloride in the solution downstream of a bifurcation connecting outlet line 213 to medical fluid line 19. Control unit 10 may then control the flow rate through container 240 based on signals provided by sensor 14, indicating sodium chloride concentration, in order to achieve and maintain a predetermined concentration of sodium chloride in the solution.

It is noted that the above example pertains to sodium chloride simply because dialysis fluid typically exhibits a predetermined concentration of sodium chloride (e.g. typically up to 140 mmol/l). However, the above preparation of fluid may generally comprise supply of one or more of a number of substances, including, but not limited to: NaCl, CaCl, KCL, MgCl, acetic acid, dextrose, and NaHCO$_3$.

Figure 1B:
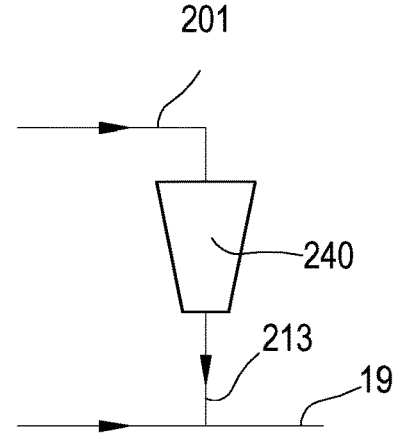
FIG. 1B schematically shows a second example of a fluid preparation apparatus 200 and a corresponding circuit, in which source fluid is drawn from a separate fluid source.

FIG. 1B schematically shows a second example of a medical fluid preparation apparatus 200 and a corresponding circuit, in which source fluid is drawn from a separate fluid source. In the second example, the apparatus for preparation of medical fluid generally operates in the same manner as described above with respect to the first example and FIG. 1A. However, in the second example, the source fluid (e.g. water) is not drawn from medical fluid line 19, but instead received from a separate fluid source (e.g. fluid line or tank). In the second example, inlet line 211 is in fluid communication with a separate source (not shown) and fluid flow is regulated in the same manner as described above with respect to the first example. Outlet line 213 is in fluid communication with medical fluid line 19 in the same manner as described above and the solution prepared is supplied to medical fluid line 19 in the same manner as describe above.

It is noted that multiple apparatuses 200 may be arranged along medical fluid line 19 in order to prepare a fluid comprising the desired substances at the desired concentrations. Accordingly, multiple apparatuses 200 may be arranged in sequence or parallel to one another, in order to control the concentration of each substance and in order to supply a desired amount of fluid at a desired flow rate. It is noted that additional component(s) (e.g. sensors, pumps, containers, etc.) may be provided and combined in a common circuit as desired in order to prepare the fluid.

FIG. 2 schematically shows a first embodiment of a coupling system for a container 240 in accordance with the present invention. Support structure 101 carries inlet line 211 and outlet line 213, as well as a bypass line 212. Further, support structure carries medical fluid line 19 and, if present, corresponding inlet and outlet ports (not shown) of medical fluid line 19. Support structure 101 further carries movable members 220 and 220', pivotably mounted to support structure 101. In FIG. 2, movable members 220 and 220' are both shown in an operating position in which a container 240 is coupled with its upper and lower ends to the two movable members 220 and 220', respectively. It is noted that "upper" and "lower" refers to a use connotation in which fluid enters container 240 at the upper end thereof (near the top of FIG. 2) and exits container 240 at a lower end thereof (near the bottom of FIG. 2). It is, however, understood that the coupling system may have a different configuration (e.g. having ports at the same level or at any angle between and including vertical and horizontal fluid flow). In this shown configuration, fluid is supplied to container 240 through inlet line 211 and exits container 240 through outlet line 213 in order to dissolve or otherwise introduce one or more substances into the fluid supplied (see above).

In order to couple container 240 to movable members 220 and 220', movable member 220 can be brought into a coupling configuration CC (indicated by a dashed line showing an inclined orientation), in which a first port 221 (e.g. coupling outlet port 221) carried by movable member 220 is in a spaced apart position relative to a third port 223 (e.g. coupling inlet port 223) carried by movable member 220'. In the coupling configuration CC, a distance between coupling ports 221 and 223 is larger than a distance between corresponding inlet and outlet ports 241 and 242 (i.e. first 241 and second 242 connection ports), which are carried by container 240 and are configured to connect to coupling ports 221 and 223. In this configuration, container 240 can be placed on movable member 220' by an operator in such a manner that outlet port 242 of container 240 connects to coupling inlet port 223 of movable member 220' in a way providing for a sealed connection between ports 242 and 223 that brings an inner volume of container 240 into fluid communication with outlet line 213. Subsequently, the operator positions container 240, still connected to outlet port 213, so that inlet port 241 of container 240 is in superimposition with (i.e. vertically below) coupling outlet port 221 of movable member 220. The operator then pivots movable member 220 downward from the inclined position indicated by the dashed line in FIG. 2, thereby bringing coupling outlet port 221 towards inlet port 241 and in contact therewith. When movable member 220 has been brought into the operating configuration shown in FIG. 2, the connection between ports 221 and 241, and ports 223 and 242, respectively brings inlet line 211 into fluid communication with the inner volume of container 240 and further into fluid communication with outlet line 213.

It is understood that movable member 220 may be locked intermittently in the coupling configuration CC and in the operating configuration OC. Alternatively, movable member 220 may require manual interaction by the operator in order to maintain the coupling configuration so that upon release movable member 220 returns to its operating configuration and an incomplete coupling (e.g. only of ports 223 and 242) is prevented. Further, it is understood that the locking of movable member(s) 220 and 220' in the operating configuration may be achieved by a mechanical (or other) locking action between ports 221 and 241, and between ports 223 and 242, respectively.

Additionally or alternatively, movable members 220 and 220' may exhibit separate locking means (e.g. in connection with their respective movable coupling to support structure 101) that ensure locking of movable members 220 and 220' in the operating configuration. For example, movable members 220 and 220' may comprise a pivoting joint operably coupled to support structure 101 with a bearing that facilitates releasable engagement of the respective moveable member in a number of distinct positions or orientations. The movable members may then snap into position in the operating configuration OC, in the coupling configuration CC, or in any other configuration (i.e. comprising a predetermined position or orientation with respect to support structure 101) as desired. When movable member 220 snaps into position in the coupling configuration CC, an operator can easily and accurately couple a container 240 to the apparatus 200, starting with outlet port 242 engaging coupling inlet port 223 of movable member 220', then positioning container 240 such that inlet port 240 is substantially in alignment with coupling outlet port 221, and then bringing movable member 220 from the coupling configuration (which movable member 220 maintained as described above) into the operating configuration.

When coupling container 240 to the coupling system, typically seals covering ports 241 and 242 of container 240 are pierced or otherwise perforated only during coupling in order to prevent contents from spilling beforehand. For example, coupling inlet port 223 may comprise a piercing element configured to pierce a seal (e.g. a membrane or film) present at port 242 of container 240 during placement of container 240 upon movable member 220'. This ensures that container 240 is securely placed on movable member 220' and that, consequently, ports 242 and 223 are securely connected. Similarly, port 221 may contain a piercing element interacting in the same manner with a seal present at port 241 of container 240. It is noted that container 240 may comprise additional covers (e.g. caps) on ports 241 and 242 during shipping or storage, which can be removed by an operator prior to coupling.

Figure 2B:
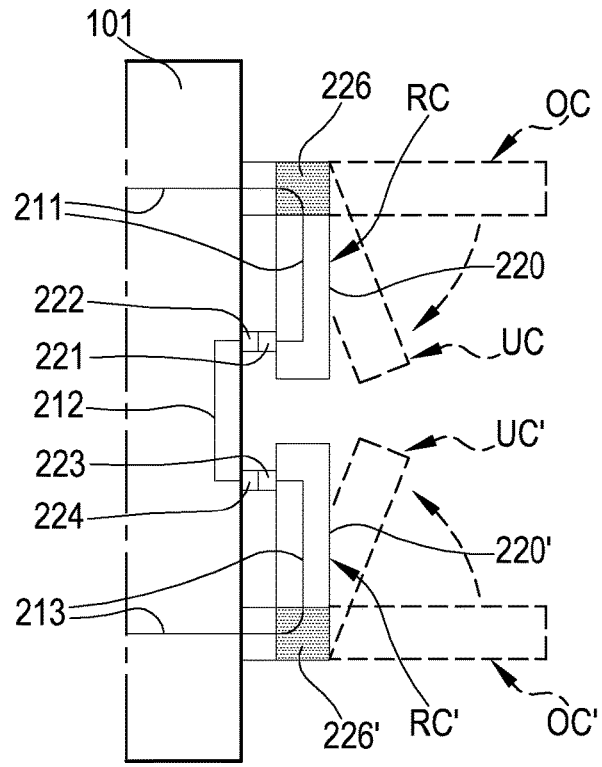

FIGS. 2A and 2B schematically show movable members 220 and 220' in an operating configuration (see FIG. 2A) and in a retracted configuration (FIG. 2B). Further, FIG. 2B schematically shows movable members 220 and 220' in their respective operating configurations OC and unretracted configurations UC (see dashed lines marked OC and UC, and OC' and UC', respectively).

The operating configuration OC and the coupling configuration CC have been described above with respect to FIG. 2. FIG. 2A shows container 240 operably coupled to apparatus 200 through movable members 220 and 220' in their respective operating configurations OC and OC'.

FIG. 2B schematically shows how movable members 220 and 220' can be brought into a retracted configuration RC after use. In FIG. 2B, container 240 has been removed in a process essentially corresponding to the coupling process detailed above, performed by an operator substantially in reverse to what has been described above. In short, upon depletion of container 240 or at the end of fluid preparation or treatment, movable member 220 is brought into the coupling configuration CC, in which ports 221 and 241 are spaced apart from each other and in which the operator can remove container 240 by moving container 240 upward from movable member 220' and outward and away from support structure 101.

Subsequently, movable members 220 and 220' are brought into their respective retracted configurations RC, in order to close the preparation circuit comprising fluid lines 211, 212, and 213, for example for the purpose of disinfection, cleaning, priming, or storage. Similarly, movable members 220 and 220' may be brought into their respective operating configurations OC and OC' before use.

As illustrated in FIG. 2B (see dashed lines), movable members 220 and 220' may be brought from their respective operating configurations OC into an unretracted configuration UC, in which movable members 220 and 220' are close to support structure 101, but not fully retracted and locked therewith, and finally into a retracted configuration RC in which movable members 220 and 220' are fully retracted towards support structure 101 and in locked engagement therewith.

As shown, movable members 220 and 220' may be coupled to support structure 101 in a manner facilitating pivoting movement of the respective member with respect to the support structure 101, as illustrated in FIGS. 2A and 2B. The pivoting joint may be configured to provide a latching or catching of the movable member in particular orientations. For example, movable members 200 and 220' may be configured to pivot with respect to support structure 101 in a manner that allows for movable member 220 and 220' to resist pivoting out of their respective operating configuration OC, for example towards the unretracted configurations UC and UC'. This mechanism can ensure that an operator has to manually move or pivot movable members 220 and 220' in a conscious manner and thereby prevent unintentional movement or adjustment of movable members 220 and 220' (e.g. by force of gravity, vibration, or accidental contact or interaction).

The process of retracting a movable member is described with respect to movable member 220. It is noted that an interaction with movable member 220' is substantially identical. However, it is noted that in some embodiments, movable member 220' cannot be brought into a coupling configuration corresponding coupling configuration CC' of movable member 220, for example when it is desired that movable member 220' provides a secure resting abutment for container 240 during coupling and operation.

An operator manually moves movable member 220 from its operating configuration OC (or any other position, e.g. when movable member is in its coupling configuration CC) towards the unretracted configuration, typically overcoming one or more releasable engagements (i.e. resisting initial or further movement at predetermined positions/configurations) of movable member 220 as described above. In the unretracted configuration UC, movable member 220 is in a position with respect to support structure 101 that facilitates visual verification of the configuration that movable member has been brought into. This means that the operator can easily distinguish between, for example, movable member 220 being in its unretracted configuration UC and movable member 220 being in its retracted configuration RC. In the unretracted configuration UC, movable member 220 is still in a position where coupling outlet port 221 is spaced apart from bypass inlet port 222 (both ports are only shown in the retracted configuration RC in FIG. 2B for clarity). The operator manually moves movable member 220 from its unretracted configuration UC into its retracted configuration RC, in which a proper connection between coupling outlet port 221 and bypass inlet port 222 is achieved. Movable member is then locked in the retracted configuration RC.

Figure 3A:
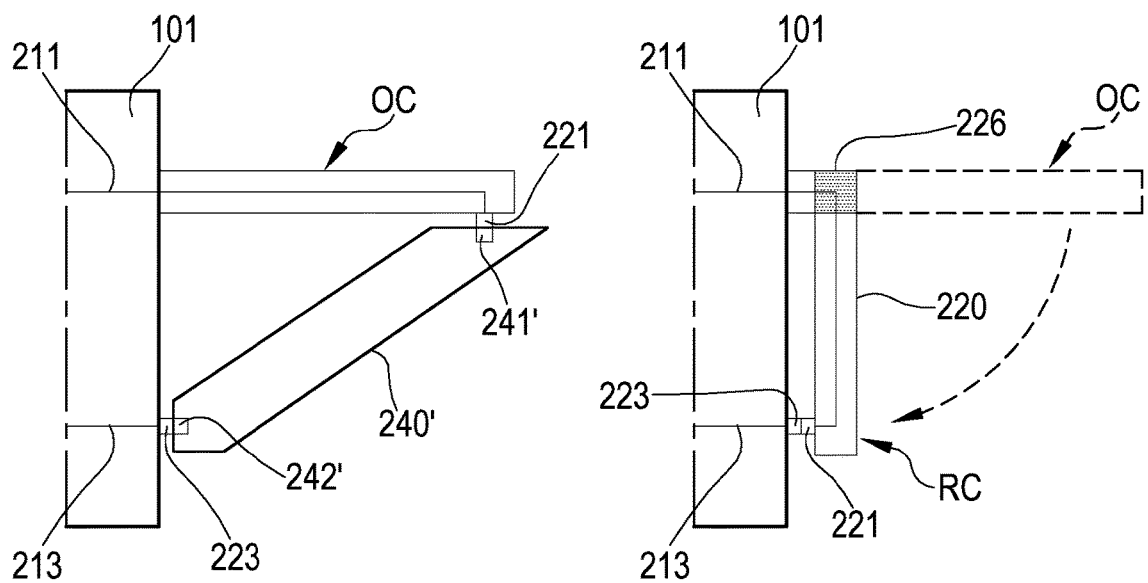
FIGS. 3A, 3B, and 3C schematically show embodiments comprising a single movable member 220 in an operating configuration (see left hand side of each figure) and in a retracted configuration (see right hand side of each figure)
Figure 3B:
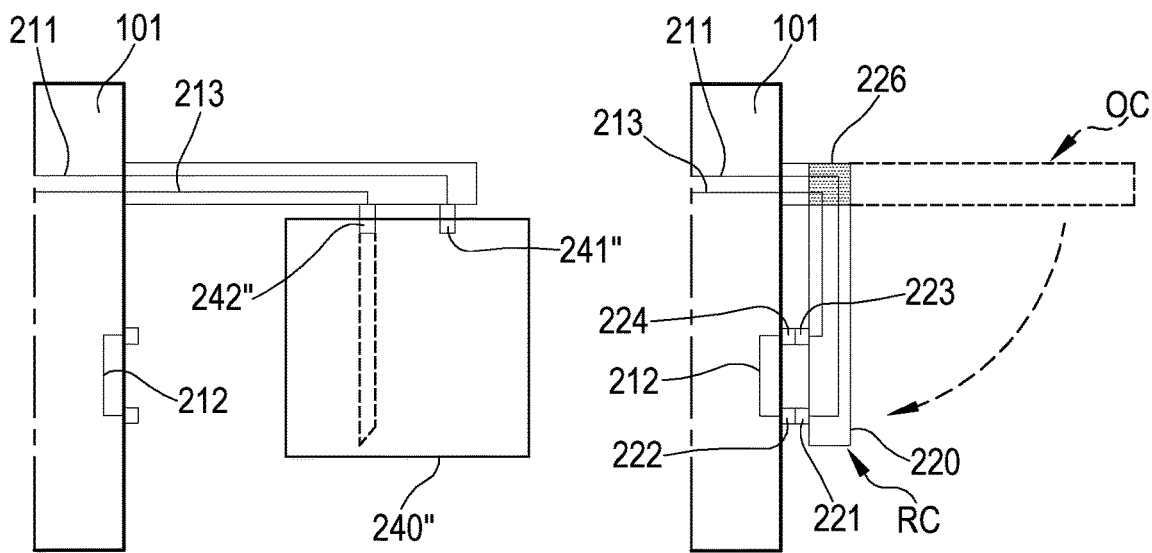
Figure 3C:
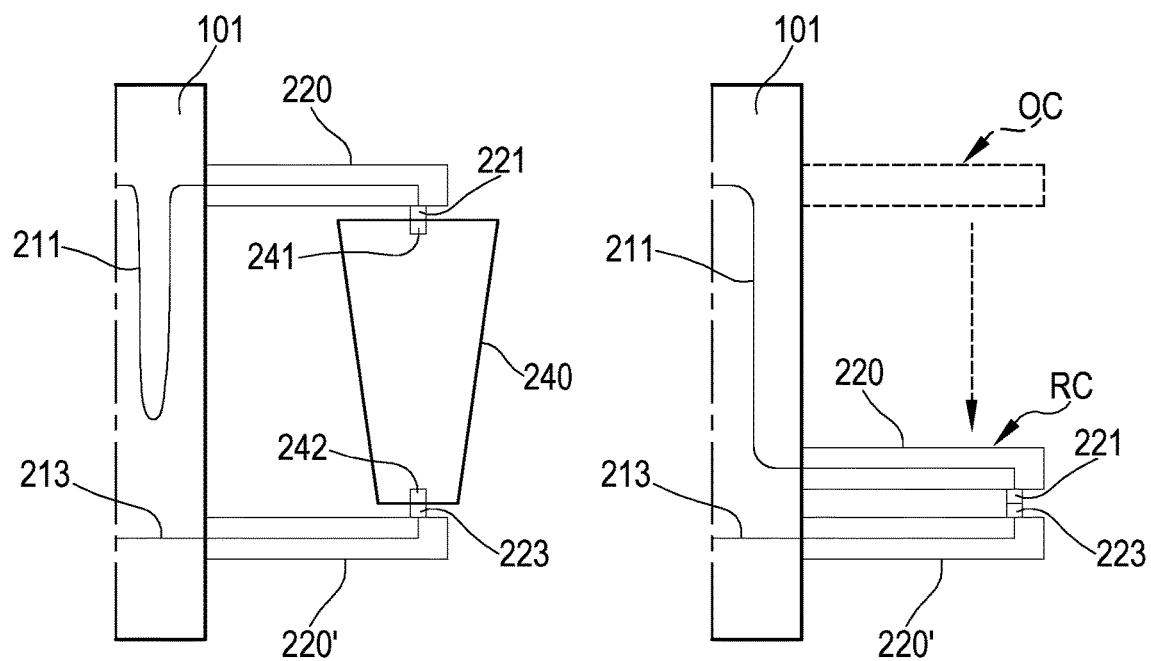

FIGS. 3A, 3B, and 3C schematically show embodiments comprising a single movable member 220 in an operating configuration (see left hand side of each figure) and in a retracted configuration (see right hand side of each figure).

FIG. 3A shows an exemplary embodiment in which a container 240' is coupled with a single movable member only. Container 240' is similar to above-described containers 240, except for a particular arrangement of the outlet port 242'. Here, outlet port 242' is arranged at a lower side surface of container 240', thereby facilitating coupling of port 242' directly with port 223 arranged on support structure 101 (not necessitating a bypass line 212, because outlet line 213 can be directly connected to either port 242' or port 221. This embodiment allows for coupling of a container 240' using only a single movable element 220.

FIG. 3B shows an exemplary embodiment in which a container 240" is coupled with a single movable member only. Container 240" differs from above-described containers 240, 240' in that both inlet and outlet ports 241" and 242" are arranged on the same (upper) end of container 240" in order to interact with two coupling ports 221 and 223, both carried by a single movable member 220. This embodiment allows for coupling of a container 240" using only a single movable element 220. Further, when container 240" is not entirely depleted upon uncoupling, the danger of its contents spilling is substantially reduced, due to inlet and outlet ports 241" and 242" being arranged at the upper end of container 240".

FIG. 3C shows an exemplary embodiment similar to the embodiment shown in FIG. 2 in which a movable member 220 is configured to vertically translate with respect to a member 220' in order to facilitate a direct connection between coupling ports 221 and 223 without necessitating a bypass line. In this embodiment, container 240 corresponds to containers 240 a described above. However, movable member 220 is capable of translating vertically, such that direct contact between ports 221 and 223 can be achieved. In this manner, the presence of a bypass line 212 is not required.

It is noted that, in addition to the embodiments described above, alternative embodiments having one or two movable members are possible. In all embodiments, however, the position of at least one movable member has to be accurately and reliably detected. This is achieved using a coupling system in accordance with the present invention.

Figure 4:
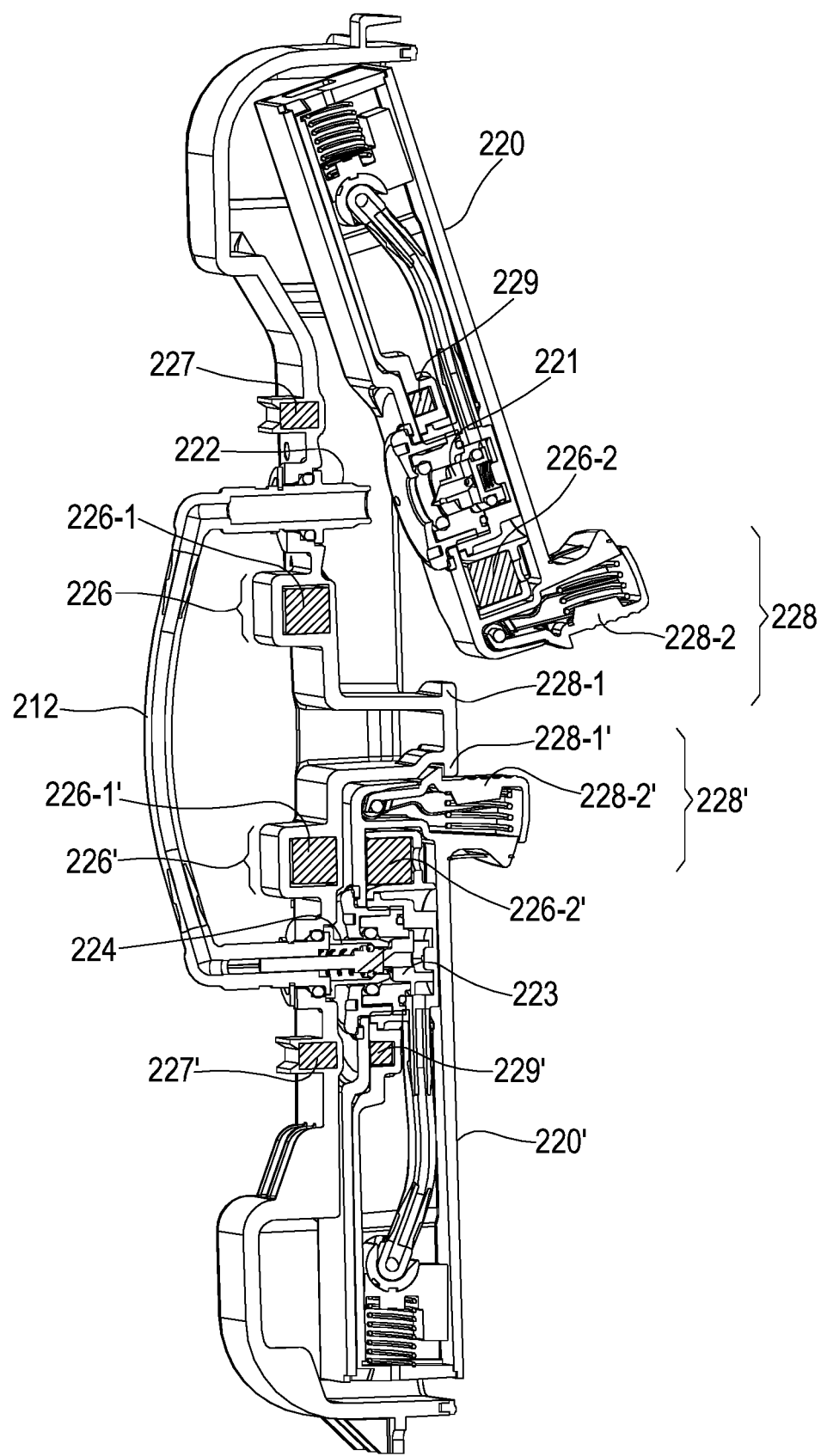
FIG. 4 shows a cross section of the first embodiment of a coupling system for a container 240 in accordance with the present invention.

FIG. 4 shows a cross section of the first embodiment of a coupling system for a container 240 in accordance with the present invention. For clarity, FIG. 4 shows movable members 220 and 220' in different configurations. Movable member 220 is shown in its unretracted configuration UC and movable member 220' is shown in its retracted configuration.

The coupling system comprises biasing means 226 configured to exert a biasing force on movable member 220. The coupling system further comprises locking means 228 configured to releasably lock movable member 220 in its retracted configuration. For clarity, the operation and functionality of the biasing means and the locking means is described primarily with respect to movable member 220 and biasing means 226 as well as locking means 228, respectively. It is understood that that biasing means 226' and locking means 228' interact with movable member 220' in an essentially identical manner, unless expressly noted otherwise.

The biasing means may operate in at least one of a repulsion mode and an attraction mode. In their repulsion mode, the biasing means are configured to exert a repulsion force directing the respective movable member away from its retracted configuration. In their attraction mode, the biasing means are configured to exert an attraction force directing the respective movable member towards its retracted configuration. The repulsion mode and the attraction mode of the biasing means are described in detail below. It is noted that both modes facilitate that a respective movable member is prevented from staying in an intermediate configuration between its unretracted configuration and its retracted configuration. This means that a respective movable member is either pushed away (e.g. repulsed) from its retracted configuration or pulled (e.g. attracted) towards its retracted configuration.

Locking means 228 are configured to releasably hold movable member 220 in its retracted configuration RC. When movable member 220 is actuated by an operator and moved towards and into its retracted configuration RC, locking means 228 are configured to deploy (i.e. engage or lock) and to prevent movable member 220 from returning, for example, into its unretracted configuration UC (or from otherwise leaving its retracted configuration RC). Upon interaction by an operator, locking means 228 are configured to disengage and to release movable member 220 from its retracted configuration RC.

In the following, the functionality of biasing means 226 are described, when they are in their repulsion mode. Biasing means 226 are configured to at least exert a biasing force upon movable member 220 when locking means 228 release movable member 220 from its retracted configuration RC. In some embodiments, biasing means 226 may be configured to permanently exert a biasing force upon movable member 220, irrespective of the locking means 228 locking movable member 220 in its retracted configuration RC. Biasing means 226 are configured to exert a biasing force upon movable member 220 in order to achieve multiple effects in their repulsion mode.

A first effect includes that movable member 220, when locking means 228 release movable member 220 from its retracted configuration RC, cannot maintain the position or orientation comprised in the retracted configuration RC, but instead is directed away from the retracted configuration RC by the biasing force exerted by biasing means 226. In some embodiments, movable member 220 is not only directed away from its retracted configuration RC but towards or into its unretracted configuration UC. Therefore, due to the biasing force exerted by biasing means 226, movable member 220 will always move away from its retracted configuration RC upon release, unless movable member 220 is locked in its retracted configuration RC by locking means 228.

In this respect, biasing means 226 are configured to exert a biasing force upon movable member 220 that is large enough to overcome any static friction or dynamic friction caused by a connection between the respective ports (e.g. ports 221 and 222). In particular, the biasing force is large enough to also overcome potential static cohesion (or stiction) caused by the connection of the respective ports. It is known that solid objects pressing against each other (in absence of relative motion) require some threshold of force parallel to the surface of contact in order to overcome static cohesion or stiction. This effect typically entails a spike in the force required to overcome stiction, without an increased force being necessary any more, as soon as dynamic friction (in the presence of relative motion between the objects) is achieved. Depending upon the individual shape or form of the respective ports, or depending upon the connection mechanism, static cohesion may or may not be a factor upon release of movable member 220.

It is noted that the mode of connection between the respective ports may support or counteract the biasing force. In some embodiments, the connection between the respective ports requires additional force during connection and disconnection in order to provide a particularly good connection (e.g. hermetically sealed, suitable for high pressures, etc.) due to additional force required to engage or disengage the connection. In other embodiments, the connection between the respective ports is substantially achieved by movable member 220 biasing corresponding (elastic) port elements against each other in the retracted configuration RC. This may entail, for example, contact surfaces of corresponding ports contacting each other and elastic portions of the corresponding ports deforming and thereby providing a compressive force maintaining a desired connection between the ports. In general, movable member 220 biasing corresponding (elastic) elements of the respective ports against each other may ensure both a secure connection as well as that movable member 220 is reliably directed away from the retracted configuration RC upon release by the locking means. In individual and very specific embodiments, the biasing means may consist solely of elastically deformable port elements exerting the biasing force upon movable member 220.

A second effect includes that an operator is required to exert a pushing force upon movable member 220, which is larger than the biasing force, in order to be able to move movable member 220 into its retracted configuration RC, for example from its unretracted configuration UC, thereby overcoming the biasing force. In addition, as described above, in some embodiments it might be required to overcome also a force exerted by elastic deformation of respective port elements (see deformable ports as discussed above). This, generally, ensures that movable member 220 cannot accidentally be moved, for example from the unretracted configuration UC, towards or into the retracted configuration RC or into a configuration similar to the latter. Instead, a particular interaction by an operator is required to intentionally move movable member 220.

The embodiment shown in FIG. 4 illustrates exemplary magnetic biasing means 226 and exemplary mechanical locking means 228. It is understood that both means 226 and 228 may be realized in a different manner, depending upon individual requirements. Such alternative embodiments include, but are not limited to mechanical mechanisms (e.g., springs, elastically deformable elements), magnetic means (e.g. magnets, solenoids). Some examples are described further below.

Biasing means 226 as shown in FIG. 4 comprise portions 226-1 and 226-2. Static portion 226-1 is carried by support structure 101 and may be arranged as an embedded element within support structure 101 as illustrated in FIG. 4. It is noted that portion 226-1 may be "static" merely in the sense that it is arranged on the support structure and not on the movable member, such that the term is not intended to be limiting. Corresponding portion 226-2 is carried by movable member 220 and may be arranged as an embedded element within movable member 220. It is noted that an element being embedded may include the element being integrated into some component such that the element is covered by an outside surface of the component. Alternatively, the outside surface may comprise at least part of the element, for example when the element provides an outer surface co-planar to the outside surface of the component. Portions 226-1 and 226-2 being embedded within respective support structures may provide the advantage of maintaining a sealed surface (e.g. of support structure 101 or movable member 220), which is easier to keep clean or provides a smooth outer surface. It is understood that portions 226-1 and 226-2 may be arranged on or in the respective structures in any manner, provided that a desired spatial relationship between the two portions is achieved.

Portions 226-1 and 226-2 comprise bar magnets arranged with respect to support structure 101 and movable member 220, respectively, in a manner that allows for both portions 226-1 and 226-2 to be positioned with respect to each other in a predetermined spatial relationship when movable member 220 is in its retracted configuration RC and in a different predetermined spatial relationship when movable member 220 is in its unretracted configuration UC. When movable member 220 is in its retracted configuration RC, portions 226-1 and 226-2 are in close proximity to each other, thereby allowing for magnetic biasing between the two portions 226-1 and 226-2. This is facilitated on one hand by the proximity of the two portions 226-1 and 226-2 and on the other hand by portions 226-1 and 226-2 being arranged with their identical poles facing each other. As shown, portion 226-1 is arranged with its south pole facing towards portion 226-2, and portion 226-2 is arranged with its south pole facing towards portion 226-1 (it is noted that the polarity may also be reversed; e.g. north poles facing each other). In close proximity, both portions 226-1 and 226-2 create a magnetic biasing force acting upon both portions and forcing them apart, thereby creating the biasing force acting between support structure 101 and movable member 220. Upon movable member 220 being directed away from the retracted configuration RC (due to the biasing force between portions 226-1 and 226-2), the spacing between both portions 226-1 and 226-2 increases and the magnetic biasing (i.e. the repulsion force) decreases. Both portions 226-1 and 226-2 may be configured to exert any desired biasing force (or repulsion force) based on one or more of their respective dimensions, size, relative spacing, orientation, relative positioning, etc.

Locking means 228 as shown in FIG. 4 comprise portions 228-1 and 228-2. Static portion 228-1 is carried by support structure 101 and may be realized as an integrally-formed element within support structure 101 as illustrated in FIG. 4. With respect to the term "static" it is referred to the description of element 226-1 above. In the embodiment shown, portion 228-1 comprises a projection integrally formed with support structure 101. Corresponding portion 228-2 is carried by movable member 220 and comprises a pivotable locking element and a spring element biasing the pivotable locking element in an outward position that allows for locking engagement with corresponding portion 228-1 when movable member is in its retracted configuration RC. The pivotable locking element further comprises an actuation surface that allows for an operator to temporarily pivot the pivotable element towards a position facilitating disengagement between portions 228-1 and 228-2.

It is noted that portion 228-2 need not necessarily be pivotable, but may alternatively be realized as a slidable or rotatable locking element, capable of corresponding movement (or as an element capable of any other suitable movement).

In FIG. 4, movable member 220 is shown in its unretracted configuration UC, while movable member 220' is shown in its retracted configuration RC.

An operator may interact with movable member 220 in a manner pushing movable member 220 towards and into its retracted configuration RC. This interaction results in ports 221 and 222 being connected, thereby putting inlet line 211 and bypass line 212 into fluid communication with each other. Further, portions 226-1 and 226-2 of biasing means 226 are brought into proximity to one another, thereby creating or increasing a biasing force directing movable member 220 away from its retracted configuration RC (not effecting a corresponding movement due to the operator's interaction). And portions 228-1 and 228-2 of locking means 228 engage with one another upon movable member 220 reaching its retracted configuration RC, thereby preventing movable member 220 from leaving its retracted configuration RC when the operator ceases the interaction (e.g. when the operator stops pushing movable member 220 towards its retracted configuration RC)—even though the biasing force is still present. Movable member 220, at the end of the interaction, may then be in its retracted configuration RC (corresponding to what is shown in FIG. 4 for movable member 220').

Likewise, an operator may interact with movable member 220' in a manner disengaging locking means 228' by pressing on an actuation surface of portion 228-2' of locking means 228'. Due to the biasing force created by the proximity of portions 226-1' and 226-2' of biasing means 226', movable member 220' is then directed away from its retracted configuration RC', optionally guided by a pushing force exerted by the operator (the pushing force being smaller than the biasing force in order to allow for movable member 220' to move towards and into its unretracted configuration UC'). As portions 226-1' and 226-2' become increasingly spaced apart, the biasing force exerted by portions 226-1' and 226-2' decreases and may cease altogether upon movable member 220' reaching its unretracted configuration UC'. Movable member 220', at the end of the interaction, may then be in its unretracted configuration UC' as shown in FIG. 4 for movable member 220.

It is understood that both movable members 220 and 220' can be moved back and forth between the respective configurations (e.g. RC, RC', UC, UC', OC, OC', or CC) as desired. The above-described interaction is exemplary and not intended to limit an operator's options when interacting with movable members 220 and/or 220'.

In the following, the functionality of biasing means 226 are described, when they are in their attraction mode. Biasing means 226 are configured to at least exert a biasing force upon movable member 220 when movable member 220 is in its unretracted configuration RC. In some embodiments, biasing means 226 may be configured to permanently exert a biasing force upon movable member 220, irrespective of movable member 220 being in its unretracted configuration UC. Biasing means 226 are configured to exert a biasing force upon movable member 220 in order to achieve multiple effects in attraction mode.

A first effect includes that movable member 220, when movable member 220 is in its unretracted configuration RC, cannot maintain the position or orientation comprised in the unretracted configuration UC, but is instead directed away from the unretracted configuration UC by the biasing force exerted by biasing means 226.

A second effect includes that movable member 220 is not only directed away from its unretracted configuration UC but towards and into its retracted configuration RC. Therefore, due to the biasing force exerted by biasing means 226, movable member 220 will always move into its retracted configuration RC upon being brought into its unretracted configuration UC.

In this respect, biasing means 226 are configured to exert a biasing force upon movable member 220 that is large enough to overcome any (static or dynamic; see above) friction caused by a connection between the respective ports (e.g. ports 221 and 222).

In the attraction mode, biasing means 226 may be realized in a similar manner as shown in FIG. 4 in the repulsion mode. In an exemplary embodiment, portions 226-1 and 226-2 may comprise bar magnets arranged with respect to support structure 101 and movable member 220, respectively, in a manner similar to the repulsion mode described above. When movable member 220 is in its unretracted configuration RC, portions 226-1 and 226-2 are in close enough proximity to each other, such that a magnetic attraction force between the two portions 226-1 and 226-2 can be created. This is facilitated on one hand by the proximity of the two portions 226-1 and 226-2 and on the other hand by portions 226-1 and 226-2 being arranged with non-identical poles facing each other. Portion 226-1 may be arranged with its south pole facing towards portion 226-2, and portion 226-2 may be arranged with its north pole facing towards portion 226-1 (it is noted that the polarity may also be reversed; e.g. a north pole facing a south pole). The magnetic attraction force is large enough to move movable member 220 towards its retracted configuration. As portions 226-1 and 226-2 get closer to each another, the magnetic attraction force increases. In close proximity, both portions 226-1 and 226-2 create a magnetic attraction force acting upon both portions and forcing them together, thereby creating the biasing force acting between support structure 101 and movable member 220.

Irrespective of the operating mode of the biasing means, control unit 10 may be connected to proximity sensors (e.g. a reed switch) configured to detect the presence of movable members 220 and 220' in their respective retracted configurations. In FIG. 4, proximity sensors 227 and 227' (each comprising a reed switch) are configured to respectively detect the presence of activators 229 and 229' (each comprising a magnet) in their vicinity. In the example shown, movable member 220 carries activator 229 and is in a position in which activator 229 cannot act on (i.e. cannot activate) proximity sensor 227, because activator 229 is spaced apart from proximity sensor 227. Further, in the same example, movable member 220' carries activator 229' and is in a position in which activator 229' acts on (i.e. activates) proximity sensor 227', because activator 229' is in the vicinity of proximity sensor 227'. It is noted that an "activation" of any one of proximity sensors 227 and 227' may include opening or closing of a respective switch, both of which are detectable by control unit 10 connected to proximity sensors 227 and 227'.

As described above for their two operating modes, biasing means 226 and 226' are configured to ensure that movable elements 220 and 220' cannot remain in a configuration that would allow for an inaccurate detection of the proximity sensors. An inaccurate detection may, for example, be caused by hysteresis, wherein a detection of the presence of a movable member not only depends on the current position of the respective movable member, but also from previous movements. For example, it would be possible, due to hysteresis, that a particular position of movable member 220 while moving towards its retracted configuration RC is not detected as "proximal", while an identical position of movable member 220 while moving away from its retracted configuration RC is detected as "proximal". Biasing means 226 and 226' are, therefore, configured to ensure that movable elements 220 and 220' cannot remain in a configuration that would allow for such an inaccurate detection of the proximity sensors and ensure that movable members 220 and 220' always move at least into their respective retracted or unretracted configurations, where detection is accurate and reliable. Detection is at least accurate and reliable when movable members 220 and 220' are either locked in or attracted into their respective retracted configurations, or when they are pushed (e.g. repulsed) into their respective unretracted configurations.

In this respect, the system not only provides sensor feedback to control unit 10, but also enables an operator to clearly distinguish (e.g. visually) between the respective retracted configurations and unretracted configurations, due to the enforced discrete positioning of the movable members in their respective configurations, thereby preventing any temporary or permanent (i.e. without outside intervention) positioning between the two configurations.

Figure 5:
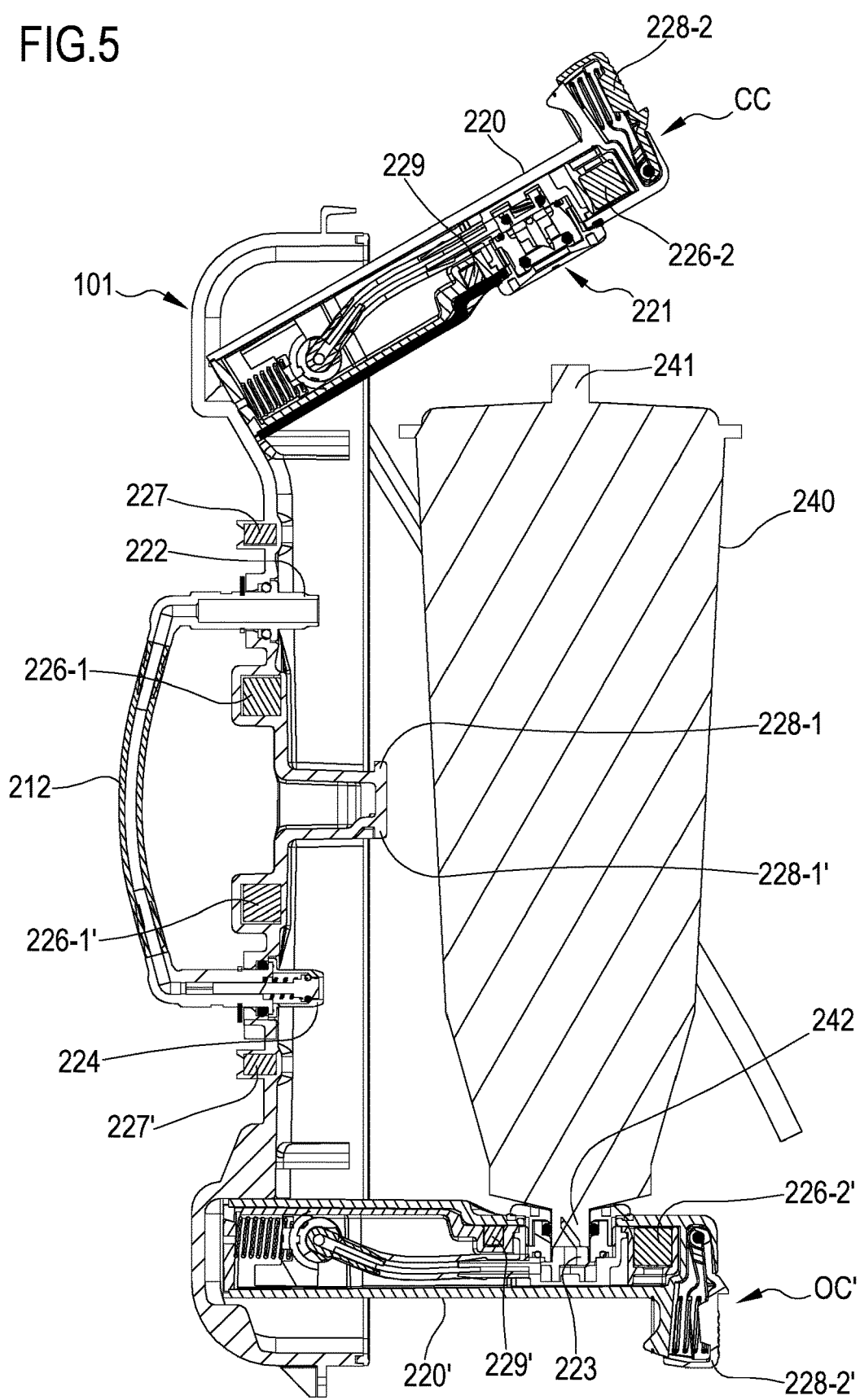
FIG. 5 shows a cross section of the first embodiment of a coupling system for a container 240 in accordance with the present invention.

FIG. 5 shows a cross section of the first embodiment of a coupling system for a container 240 in accordance with the present invention; FIG. 5 shows movable member 220 in the coupling configuration CC and container 240 also in cross section.

Figure 6:
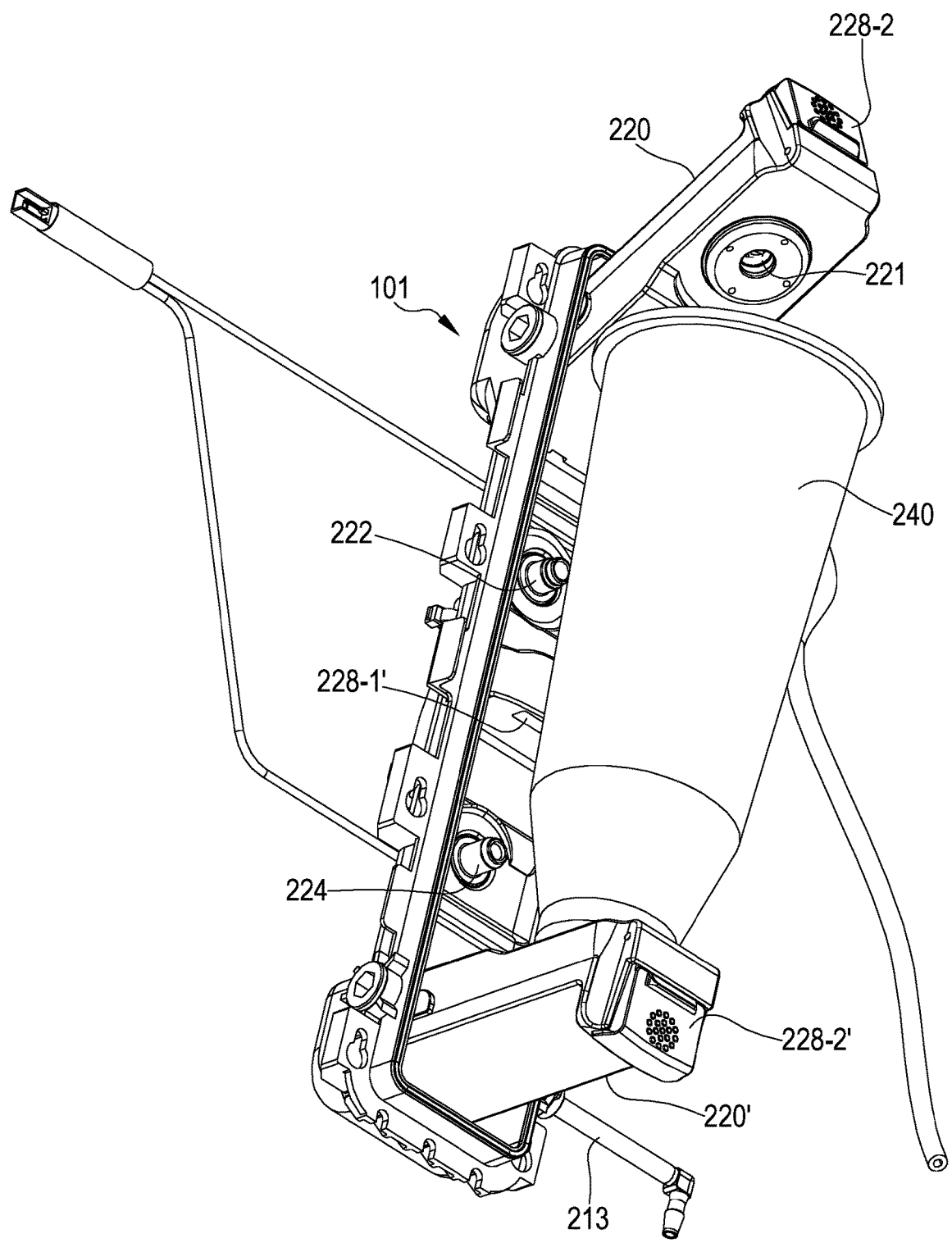
FIG. 6 shows a perspective view of the first embodiment of a coupling system for a container 240 in accordance with the present invention.

FIG. 6 shows a perspective view of the first embodiment of a coupling system for a container 240 in accordance with the present invention; FIG. 6 shows the same configuration as the cross section of FIG. 5.

Further interactions of an operator include moving movable members 220 and 220' into their respective operating configurations OC and OC'. Further, movable member 220 may be moved into its coupling configuration CC (see, e.g., FIGS. 2, 5, and 6), which allows for the coupling of a container 240 with movable members 220 and 220'.

In FIGS. 5 and 6, movable member 220 is shown in its coupling configuration CC and container 240 is shown coupled to movable member 220'. FIG. 5 also shows, in cross section, an exemplary piercing element (near outlet port 242) that is configured to pierce a seal present at outlet port 242 of container 240 as described above.

During coupling of a container 240, typically, movable member 220' remains in its operating configuration OC' (and may not even be able to assume a coupling configuration, see above) whereas movable member 220 can be brought into its coupling configuration CC, which allows for container 240 to be placed first on movable member 220' (with port 242 connecting to outlet port 223). Subsequently, movable member 220 is brought into its operating configuration OC, thereby connecting its inlet port 221 and port 241 of container 240.

FIG. 6 shows a perspective view of movable members 220 and 220', as well as container 240 and support structure 101. In particular, exemplary actuation surfaces are shown on portions 228-2 and 228-2' of locking means 228 and 228', respectively. Further, the location of bypass ports 222 and 224 is shown. Support structure 101 may be configured as a mountable unit (as shown), which can be mounted to a main body of apparatus 1.

Figure 7:
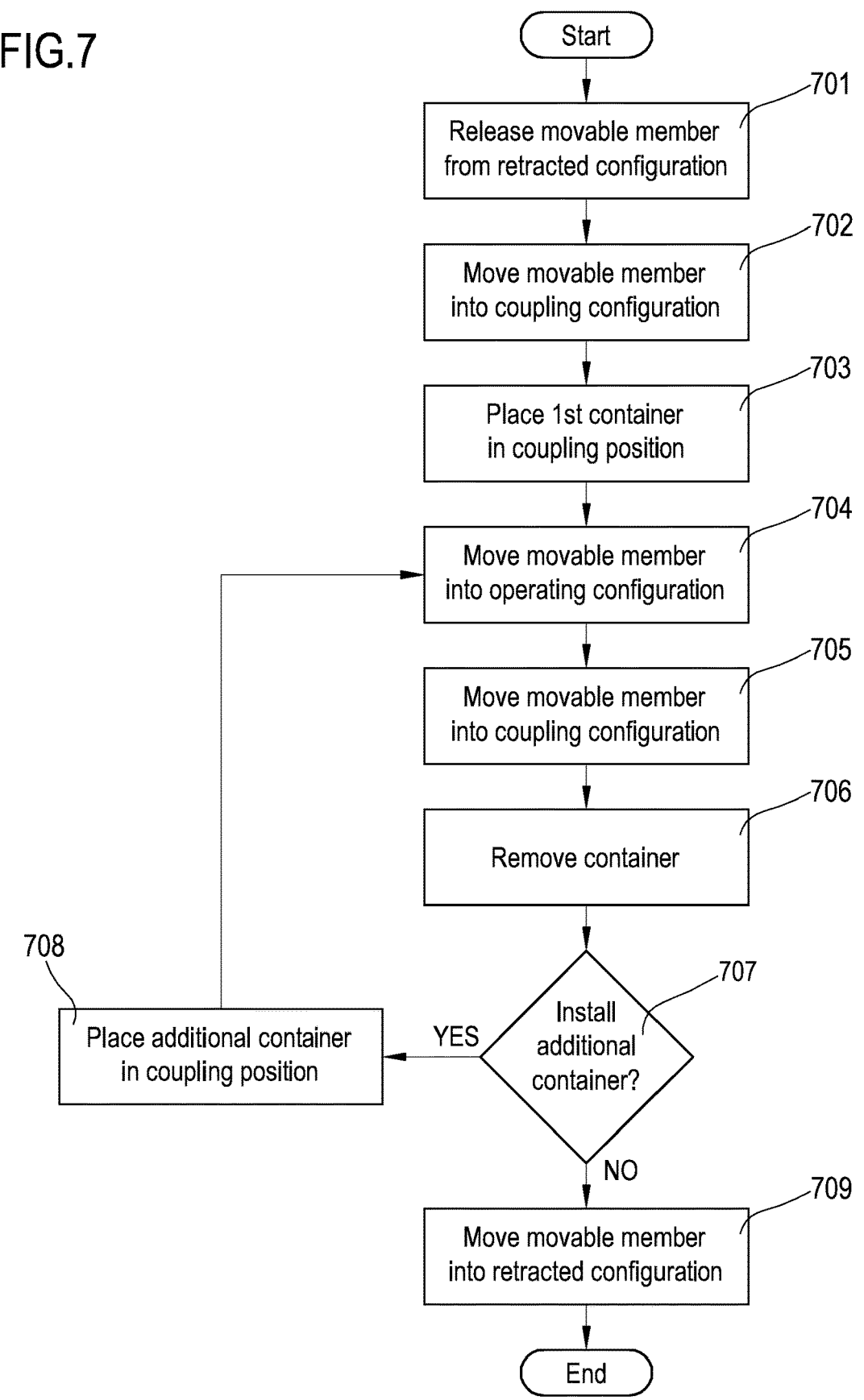
FIG. 7 shows a flow chart illustrating a process for setting up and operating a medical apparatus for the preparation of medical fluid according to the present invention.

FIG. 7 shows a flow chart illustrating a process for setting up and operating a medical apparatus for the preparation of medical fluid according to the present invention. In step 701, the movable member is released from its retracted configuration. For example, the operator acts on the corresponding locking means in order to release the movable member. In step 702, the movable member is moved into its coupling configuration. If the biasing means are operating in their repulsion mode, this step includes the movable member moving into its unretracted configuration without any interaction by the operator. As soon as the movable member is released, it is configured to move into the unretracted configuration due to the biasing force acting upon the movable member. If the biasing means are operating in their attraction mode, further interaction (e.g. in addition to releasing the movable member) may be required, for example the operator pulling the movable member from its retracted configuration and acting against the attraction force exerted by the biasing means. In step 703, a container is placed in a coupling position with respect to the movable member. In step 704, the movable member is moved from its coupling configuration into its operating configuration. After step 704 has been completed, the respective stage holding the container is ready for operation. Thus, if the medical apparatus is otherwise set up (e.g., operating parameter are properly set, lines and/or conduits are connected, other components are ready for operation), the preparation of medical fluid can commence. If the container is depleted and in need of replacement, for example, if the preparation of medical fluid is not yet finished, the operation is halted or suspended in a suitable manner, and in step 705, the movable member is moved from its operating configuration into its coupling configuration again, thereby facilitating the release of the depleted container. In step 706, the container is removed from the apparatus. Step 707 represents a decision as to whether an additional container is required, for example to continue preparation of medical fluid. If yes, a fresh container is placed in the coupling position with respect to the movable member in step 708, and again step 704 is performed, i.e. the movable member is again moved into its operating configuration. Steps 704, 705, 706, 707, and 708 may be executed repeatedly, as necessary. Alternatively, if no additional container is required, for example when the preparation of medical fluid if finished, step 709 may be executed, in which the container is not replaced, but the movable member is moved into its retracted configuration. For example, if the biasing means are in their repulsion mode, the operator brings the movable member not only into its unretracted configuration but further moves it (against the biasing means (i.e. the repulsion force) into its retracted configuration until the locking means engage. Alternatively, if the biasing means are in their attraction mode, the operator may bring the movable member into its unretracted configuration, wherein, upon reaching its unretracted configuration, the movable member is pulled by the biasing means (i.e. the attraction force) into its retracted configuration.

After the movable member has been moved into its retracted configuration, one of a priming process, a disinfection process, and a cleaning process, or another process may be initiated.

Figure 8:
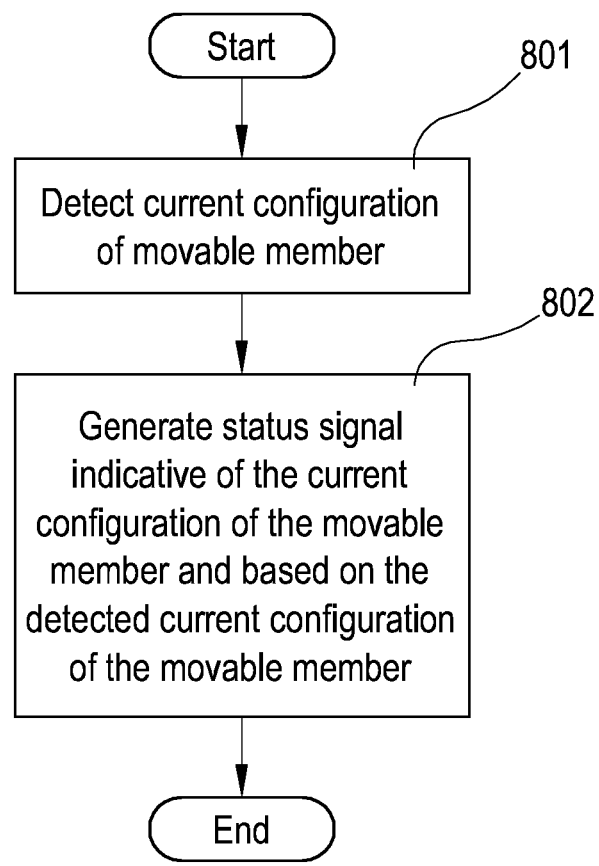
FIG. 8 shows a flow chart illustrating a process for detecting a current configuration of a movable member in a medical apparatus for the preparation of medical fluid according to the present invention.

FIG. 8 shows a flow chart illustrating a process for detecting a current configuration of a movable member in a medical apparatus for the preparation of medical fluid according to the present invention. In step 801, the current configuration of the movable member is detected. This may be performed using one or more sensors (e.g. a reed switch; see above) connected to a control unit. In step a status signal indicative of the current configuration of the movable member and based on the detected current configuration of the movable member is generated.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A medical apparatus for the preparation of medical fluid, comprising:
   a support structure;
   a movable member, movably mounted to the support structure and carrying a first port;
   a first fluid line carried by the support structure and configured to be put into fluid communication with a source of fluid, the first fluid line being in fluid communication with the first port;
   a second fluid line carried by the support structure and being in fluid communication with a second port;
   biasing means; and
   locking means;
   wherein the first port is configured to receive a first connection port of a container of at least one substance to be added to a fluid coming from the source of fluid;
   wherein the movable member is configured to move between at least a retracted configuration, in which the first port and the second port are coupled to each other, and an unretracted configuration, in which the first port and the second port are spaced apart from each other;
   wherein the locking means is configured to releasably hold the movable member in its retracted configuration when in a locked configuration;
   wherein the biasing means is configured to operate in at least one of a repulsion mode and an attraction mode, wherein in the repulsion mode, the biasing means exerts on the movable member, at least when the locking means release the movable member from its retracted configuration, a biasing force directing the movable member away from its retracted configuration, and
   wherein in the attraction mode, the biasing means exerts on the movable member, at least when the movable member is in its unretracted configuration, a biasing force directing the movable member towards its retracted configuration.

2. The apparatus of claim 1, wherein the biasing means operates only in the repulsion mode and exerts the biasing force on the movable member directing the movable member away from its retracted configuration and towards its unretracted configuration; or
   the biasing means operates only in the repulsion mode and exerts the biasing force on the movable member causing the movable member to move to its unretracted configuration when the locking means releases the movable member from the locked configuration.

3. The apparatus of claim 1, wherein, when the movable member is in its retracted configuration, the first and second ports are configured to put the first and second fluid lines in fluid communication with each other.

4. The apparatus of claim 1, wherein the biasing means comprises a first magnetic element and a second magnetic element, the first and second magnetic elements being configured to exert the biasing force.

5. The apparatus of claim 4, wherein the first magnetic element is carried by the movable member and the second magnetic element is carried by the support structure, the first magnetic element comprising a solenoid and the second magnetic element comprising a bar magnet or the first magnetic element comprising a bar magnet and the second magnetic element comprising a solenoid.

6. The apparatus of claim 1, wherein the locking means comprises a first locking element configured to selectively engage with a second locking element when the locking means is in the locked configuration, the first locking element being carried by the movable member and the second locking element being carried by the support structure, wherein at least one of the first and second locking elements is elastically biased; wherein at least one of the first and second locking elements is configured to be movable with respect to the other of the first and second locking elements to achieve selective engagement between the first and second locking elements.

7. The apparatus of claim 1, further comprising a sensor configured to generate at least a first signal when the movable member is in its retracted configuration and a second signal, different from the first signal, when the movable member is in its unretracted configuration.

8. The apparatus of claim 7, the apparatus further comprising:
   a control unit operably connected to the sensor, the control unit configured to:
   receive the first and second signals from the sensor;
   discriminate between the first and second signals; and
   generate an output signal based on the outcome of the discrimination;
   a user interface operably connected to the control unit and configured to:
   receive the output signal; and
   display an indicium indicative of a current configuration of the movable member in response to the output signal.

9. The apparatus of claim 1, wherein the movable member is configured to pivot with respect to the support structure, wherein at least a retracted angular position of the movable member relative to the support structure in its retracted configuration is different from an unretracted angular position of the movable member relative to the support structure in its unretracted configuration.

10. The apparatus of claim 1, further comprising:
    a third port carried by the movable member;
    a third fluid line carried by the support structure, the third fluid line being in fluid communication with the third port and; and a fourth port in fluid communication with the second fluid line and connected to an end of the second fluid line opposite to the second port;

wherein when the movable member is in its retracted configuration, the third port and the fourth port are in contact with each other, and when the movable member is in its unretracted configuration, the third port and the fourth port are spaced apart from each other.

11. The apparatus of claim 10, wherein, when the movable member is in its retracted configuration, the third and fourth ports put the second and third fluid lines in fluid communication with each other.

12. The apparatus of claim 10, further comprising:
a second movable member movably mounted to the support structure and carrying the third port;
second biasing means; and
second locking means;
wherein the second movable member is configured to move between at least a retracted configuration of the second movable member, in which the third port and the fourth port are connected to each other, and an unretracted configuration of the second movable member, in which the third port and the fourth port are spaced apart from each other;
wherein the second locking means is configured to releasably hold the second movable member in its retracted configuration when in a locked configuration;
wherein the second biasing means is configured to operate in at least one of a repulsion mode and an attraction mode;
wherein in the repulsion mode, the second biasing means exerts on the second movable member, at least when the second locking means release the second movable member from its retracted configuration, a second biasing force directing the second movable member away from its retracted configuration, and
wherein in the attraction mode, the second biasing means exerts on the second movable member, at least when the second movable member is in its unretracted configuration, a second biasing force directing the second movable member towards its retracted configuration.

13. The apparatus of claim 12, wherein the second biasing means operates only in the repulsion mode to exert a biasing force causing the second movable member to move away from its retracted configuration to its unretracted configuration when the second locking means releases the second movable member from the locked configuration.

14. The apparatus of claim 12, wherein, when the second movable member is in its retracted configuration, the third and fourth ports are configured to put the second and third fluid lines in fluid communication with each other.

15. The apparatus of claim 10, wherein the support structure carries the fourth port, and wherein the fourth port is configured to receive a second connection port of the container.

16. The apparatus of claim 10, further comprising a main fluid line having a first end defining a main inlet port configured to be put into fluid communication with the source of fluid and a second end defining a main outlet port, wherein the main fluid line further comprises a first bifurcation, the first bifurcation putting the first fluid line into fluid communication with the main fluid line.

17. The apparatus of claim 16, further comprising a second bifurcation putting the third fluid line into fluid communication with the main fluid line, and a second flow controller configured to control flow of fluid between the third port and the main fluid line.

18. The apparatus of claim 16, wherein the first fluid line comprises a first flow controller configured to control flow of fluid between the main fluid line and the first port.

19. The apparatus of claim 16, further comprising an output tank connected to the main outlet port and configured to collect a pre-fixed amount of fluid from the main fluid line.

20. The apparatus of claim 1, wherein the biasing means comprises a first portion and a second portion.

21. The apparatus of claim 20, wherein the first portion is carried by the support structure.

22. The apparatus of claim 20, wherein the first portion is arranged as an embedded element within the support structure.

23. The apparatus of claim 20, wherein the second portion is carried by the movable member.

24. The apparatus of claim 20, wherein the second portion is arranged as an embedded element within the movable member.

25. Method of setting up a medical apparatus for the preparation of medical fluid having:
a movable member movably mounted to a support structure and carrying a first port;
a first fluid line carried by the support structure and configured to be put into fluid communication with a source of fluid, the first fluid line being in fluid communication with the first port;
a second fluid line carried by the support structure and being in fluid communication with a second port;
wherein the movable member is mounted to the support structure for movement between at least a retracted configuration, in which the first port and the second port are coupled to each other, and an unretracted configuration, in which the first port and the second port are spaced apart from each other;
the method comprising:
locking the movable member in the retracted configuration;
releasing the movable member from its retracted configuration after locking the movable member in the retracted configuration;
biasing the movable member towards or away from the retracted configuration, wherein biasing the movable member towards the retracted configuration draws the movable member towards the retracted configuration after the movable member is released from its retracted configuration, and wherein biasing the movable member away from the retracted configuration forces the movable member away from the retracted configuration after the movable member is released from the retracted configuration;
moving the movable member into a coupling configuration after releasing the movable member from its retracted configuration;
placing a first container in a coupling position with respect to the movable member; and
moving the movable member from the coupling configuration into an operating configuration in which the first port receives a first connection port of the first container.

26. The method of claim 25, the method further comprising:
moving the movable member from its operating configuration into its coupling configuration;

removing the first container from the apparatus after moving the movable member from its operating configuration into its coupling configuration;

placing a second container in a coupling position with respect to the movable member after removing the first container from the apparatus; and moving the movable member from its coupling configuration into its operating configuration.

27. The method of claim 25, the method further comprising:

moving the movable member from its operating configuration into its coupling configuration;

removing the first container from the apparatus after moving the movable member from its operating configuration into its coupling configuration;

moving the movable member from its coupling configuration into its retracted configuration;

initiating one or more of a priming process, a disinfection process, and a cleaning process after removing the first container from the apparatus and moving the movable member from its coupling configuration into its retracted configuration.

28. An extracorporeal blood treatment apparatus, comprising:

a medical apparatus for the preparation of medical fluid the medical apparatus comprising:

a support structure;

a movable member movably mounted to the support structure and carrying a first port;

a first fluid line carried by the support structure and configured to be put into fluid communication with a source of fluid, the first fluid line being in fluid communication with the first port;

a second fluid line carried by the support structure and being in fluid communication with a second port;

biasing means; and locking means;

wherein the first port is configured to receive a first connection port of a container of at least one substance to be added to a fluid coming from the source of fluid;

wherein the movable member is mounted to the support structure for movement between at least a retracted configuration, in which the first port and the second port are coupled to each other, and an unretracted configuration, in which the first port and the second port are spaced apart from each other;

wherein the locking means is configured to releasably hold the movable member in its retracted configuration; and the biasing means is configured to operate in at least one of a repulsion mode and an attraction mode, wherein in the repulsion mode, the biasing means exerts on the movable member, at least when the locking means release the movable member from its retracted configuration, a biasing force directing the movable member away from its retracted configuration, and wherein in the attraction mode, the biasing means exerts on the movable member, at least when the movable member is in its unretracted configuration, a biasing force directing the movable member towards its retracted configuration; and a waste line connected to an outlet of a dialysis fluid chamber;

wherein the medical apparatus for the preparation of medical fluid being connected to supply fluid to at least one of a dialysis fluid line and a replacement fluid line of the extracorporeal blood treatment apparatus.

29. The extracorporeal blood treatment apparatus of claim 28, further comprising:

a dialysis fluid line configured to be connected to an inlet of a dialysis fluid chamber of a blood treatment unit; and a fluid replacement line configured to be connected to an extracorporeal blood circuit or directly to a cardiovascular system of a patient.

30. A medical apparatus for the preparation of medical fluid, comprising:

a support structure;

a movable member, movably mounted to the support structure and carrying a first port;

a first fluid line carried by the support structure and configured to be put into fluid communication with a source of fluid, the first fluid line being in fluid communication with the first port;

a second fluid line carried by the support structure and being in fluid communication with a second port;

wherein the first port is configured to receive a first connection port of a container of at least one substance to be added to a fluid coming from the source of fluid;

wherein the movable member is configured to move between at least a retracted configuration, in which the first port and the second port are coupled to each other, and an unretracted configuration, in which the first port and the second port are spaced apart from each other; and a lock configured to releasably lock the movable member in the retracted configuration;

wherein the movable member is biased away from the retracted configuration at least when the movable member is not locked in the retracted configuration, or wherein the movable member is biased towards the retracted configuration at least when the movable member is in the unretracted configuration.

* * * * *